(12) United States Patent
Neamati et al.

(10) Patent No.: US 7,928,113 B2
(45) Date of Patent: Apr. 19, 2011

(54) INTEGRIN-BINDING SMALL MOLECULES

(75) Inventors: Nouri Neamati, Fullerton, CA (US); Raveendra Dayam, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 648 days.

(21) Appl. No.: 11/559,857

(22) Filed: Nov. 14, 2006

(65) Prior Publication Data

US 2007/0155750 A1 Jul. 5, 2007

Related U.S. Application Data

(60) Provisional application No. 60/736,780, filed on Nov. 14, 2005.

(51) Int. Cl.
*A61K 31/517* (2006.01)
*A61K 31/44* (2006.01)
(52) U.S. Cl. .................. 514/266.1; 514/337
(58) Field of Classification Search .............. 514/266.1, 514/337
See application file for complete search history.

(56) References Cited

OTHER PUBLICATIONS

Edmunds, Jeremy, et al., "Derivatives of 5-[[1-(4'-Carboxybenzyl)imidazolyl]methylidene]hydantoins as Orally Active Angiotensin II Receptor Antagonists," J. Med. Chem., vol. 38, pp. 3759-3771 (1995).*
Lesyk et al., "New thiazolidones-4 with pyrazolone-5 substituent as the potential NSAIDs", Bollettino Chimico Farmaceutico, vol. 137, No. 6, pp. 210-217 (1998) abstract.*
Seada et al., "Synthesis and biological activity of some new thiazolidiones", Indian Journal of Heterocycic Chemistry, vol. 3, No. 2, pp. 81-86 (1993) abstract.*
Bhatt et al., Synthesis of anti-HIV, anticancer and antitubercular 4-oxothiazolidines, 2-imino-4-oxo-thiazolidines and their 5-arylidine derivatives, Indian Journal of Chemistry, Section B: Organic Chemistry Including Medicinal Chemistry, vol. 33B, No. 2, pp. 189-192 abstract, (1994).*
D. Schrama et al., "Antibody Targeted Drugs as Cancer Therapeutics," Nature Reviews, vol. 5, pp. 148, pp. 147-159 (2006).
R.W. Wilder, "Integrin Alpha V Beta 3 as a Target for Treatment of Rheumatoid Arthritis and Related Rheumatic Diseases," ARD Online (www.bmjjournals.com), Sep. 25, 2006.
Falm Eskens, "Angiogenesis Inhibitors in Clinical Development; Where are we now and where are we going?" British Journal of Cancer, vol. 90, pp. 1-7, (2004).
C. Ruegg et al., "Antiangiogenic Peptides and Proteins: From Experimental Tools to Clinical Drugs," Biochemical et Biophysica Acta 1765, pp. 155-177 (2006).

X. Duan et al., "Association of αvβ3 Integrin Expression with the Metastatic Potential and Migratory and Chemotactic Ability of Human Osteosarcoma Cells," Clinical & Experimental Metastatis, vol. 21, pp. 747-753 (2004).
P. Boissy et al., "Aggregation of Mononucleated Precursors Triggers Cell Surface Expression of αvβ3 Integrin, Essential to Formation of Osteoclast-Like Multinucleated Cells," Journal of Cell Science, vol. 111, pp. 2563-2574 (1998).
N. Reinmuth et al., "αvβ3 Integrin Antagonist S247 Decreases Colon Cancer Metastatsis and Angiogenesis and Improves Survival in Mice," Cancer Research, vol. 63, pp. 2079-2087 (2003).
K. Switala-Jelen et al., "The Biological Functions of β3 Integrins," Folio Biologica (Praha), vol. 50, pp. 143-152 (2004).
J. Albert et al., "Integrin αvβ3 Antagonist Cilengitide Enhances Efficacy of Radiotherapy in Endothelial Cell and Non-Small-Cell Lung Cancer Models," Int. J. Radiation Oncology Biol. Phys., vol. 65, No. 5, pp. 1536-1543 (2006).
M. Sadeghi et al., "Detection of Injury-Induced Vascular Remodeling by Targeting Activated avB3 Integrin in Vivo," Circulation (www.circulationaha.org), pp. 84-90, Jul. 6, 2004.
M. Janssen et al., "Tumor Targeting with Radiolabeled αvβ3 Integrin Binding Peptides in a Nude Mouse Model," Cancer Research, vol. 62, pp. 6146-6151 (2002).
J. Song et al., "In Vivo Characterization of the Integrin β3 as a Receptor for Hantaan Virus Cellular Entry," Experimental and Molecular Medicine, vol. 37, No. 2., pp. 121-127 (2005).
E. Toschi et al., "HIV-1 Tat Regulates Endothelial Cell Cycle Progression via Activation of the Ras/ERK MAPK Signaling Pathway," Molecular Biology of the Cell, vol. 17, pp. 1985-1994 (2006).
R. Sobel et al., "Endothelial Cell Integrin Laminin Receptor Expression in Multiple Sclerosis Lesions," American Journal of Pathology, vol. 153, No. 2, pp. 405-415 (1998).
S. Shattil et al., "Integrins: Dynamic Scaffolds for Adhesion and Signaling in Platelets," Blood, vol. 104, No. 6, pp. 1606-1615 (2004).
K. Temming et al., "RGD-Based Strategies for Selective Delivery of Therapeutics and Imaging Agents to the Tumour Vasculature," Drug Resistance Updates, vol. 8, pp. 381-402 (2005).
V. Engleman et al., "A Peptidomimetic Antagonist of the αvβ3 Integrin Inhibits Bone Resorption In Vitro and Prevents Osteoporosis In Vivo," J. Cin. Invest. vol. 99, No. 9, pp. 2284-2292 (1997).
M.Shimaoka et al., "Therapeutic Antagonists and Conformational Regulation of Integrin Function," Nature Reviews (www.nature.com), vol. 2, pp. 703-716, Sep. 2003.
V. Nguyen, "Updates on Bisphosphonates for the Treatment of Osteoporosis: Impact on Future Treatment Strategies," The Pharmacy & Therapeutics Society, Release Date: Jan. 1, 2005, Expiration Date: Dec. 31, 2005.
D. Schrama et al., "Antibody Targeted Drugs as Cancer Therapeutics," Nature Reviews, vol. 5, pp. 147-159, Feb. 2006.

* cited by examiner

*Primary Examiner* — Kevin Weddington
(74) *Attorney, Agent, or Firm* — DLA Piper LLP (US)

(57) ABSTRACT

The present invention relates to compositions containing integrin-binding small molecules. Also disclosed are methods of binding integrins to these small molecules and methods of identifying small molecules binding to integrins.

2 Claims, 11 Drawing Sheets

The $\alpha_v$ and $\beta_3$ chains of $\alpha_v\beta_3$ integrin are depicted in yellow and red respectively.

NVX-144 is shown fitting into the groove at the active binding site of the RGD tripeptide in a top view (top) and side view (bottom).

Predicted docking of NVX-188 (aqua) and the RGD tripeptide (mauve) on $\alpha_v\beta_3$ integrin. The red sphere is $Mn^{2+}$ at the binding site. The $\alpha_v$ and $\beta_3$ chains of $\alpha_v\beta_3$ integrin are depicted in green and blue respectively.

Relationship of NVX-188 (right) and a prototypic RGD-mimetic small molecule (left) to amino acids in the α$_v$β$_3$ heterodimer. The circles represent amino acids in the integrin proteins.

INTEGRIN-BINDING SMALL MOLECULES

RELATED APPLICATION

This application claims priority to U.S. Provisional Application Ser. No. 60/736,780, filed on Nov. 14, 2005, the content of which is incorporated herein by reference in its entirety.

FIELD OF THE INVENTION

The present invention relates in general to integrin-binding small molecules. More specifically, the invention provides novel compositions and methods of using these compositions for treating various diseases.

BACKGROUND OF THE INVENTION

Integrins, a family of transmembrane adhesion receptors are principal mediators of cell attachment, migration, differentiation, and survival.[1] Structurally, integrins are heterodimeric receptors that are composed of large extracellular domains, one transmembrane helix, and small intracellular domains for each subunit.[2] These receptors consist of an α- and a β-subunit, which associate non-covalently in defined combinations. To date, 18 α-subunits and 8 β-subunits have been identified, which associate selectively to form at least 24 integrins. In addition to their adhesive functions, integrins transduce messages via various signaling pathways and influence proliferation and apoptosis of tumor cells, as well as of activated endothelial cells.[3, 4] Unique combination of integrins on the cell surface allows cells to recognize and then respond to a variety of extracellular ligands. Integrin $\alpha_v\beta_3$ is a prominent member of integrin family. It has been implicated in the pathophysiology of malignant tumors where it is required for tumor angiogenesis[5] and is highly expressed on both endothelial cells in neovasculature and highly aggressive human carcinomas. Integrin $\alpha_v\beta_3$ mediates adhesion of tumor cells on a variety of extracellular matrix proteins, allowing these cells to migrate during invasion and extravasation.[6, 7] In breast cancer, $\alpha_v\beta_3$ characterizes the metastatic phenotype, as this integrin is upregulated in invasive tumors and distant metastases.[8-10] Antagonism of integrin $\alpha_v\beta_3$ is therefore expected to provide a novel approach for the treatment of metastatic and invasive cancers.[11, 12] The combination of $\alpha_v\beta_3$ antagonists with conventional treatment modalities could increase the efficacy of the metastatic cancer therapy without additional toxicity. The $\alpha_v\beta_3$ receptor binds to a variety of extracellular matrix proteins, including fibrinogen, fibronectin, osteopontin, thrombospondin, and vitronectin largely through interaction with the Arg-Gly-Asp (RGD) tripeptide sequence.[13, 14] Previously, a variety of peptidomimetic small molecule $\alpha_v\beta_3$ antagonists have been identified, some of which are active in disease models such as osteoporosis and skeletal metastatic breast cancer.[12, 15-18]

The $\alpha_v\beta_3$ antagonists potently inhibit angiogenesis in a number of animal models, including mouse xenograft models, and metastases models. Inhibition of $\alpha_v\beta_3$ activity by mAbs and cyclic RGD peptides has been shown to induce endothelial apoptosis, and inhibit angiogenesis.[19, 20] The $\alpha_v\beta_3$ antagonists can induce apoptosis not only in activated endothelial cells but also in $\alpha_v\beta_3$-positive tumor cells, resulting in a direct cytotoxic effect on tumor cells.[21] Antagonism of $\alpha_v\beta_3$ activity has resulted in decreased tumor growth in breast cancer xenografts and melanoma xenografts.[22, 23] Cilengitide, a cyclic RGD peptide in clinical trials for metastatic cancer,[24] has been tested in an aggressive breast cancer model where it was shown that the combination of Cilengitide with radioimmunotherapy remarkably enhanced efficacy and increased apoptosis, compared with single-modality therapy with either agent, without additional toxicity.[25] This suggests a real therapeutic potential of Cilengitide specifically, and $\alpha_v\beta_3$ antagonists in general, in combination anticancer therapy.

The $\alpha_v\beta_3$ receptor also plays a pivotal role in bone resorption. Various studies have indicated that $\alpha_v\beta_3$ receptor is the most abundant integrin in osteoclasts.[26-29] $\alpha_v\beta_3$ antibodies, RGD peptides, and peptidomimetic antagonists were shown to inhibit bone resorption in vivo without notable adverse affects.[30-34] On the basis of these studies, and results from initial clinical trials, $\alpha_v\beta_3$ antagonists show great promise for the treatment and prevention of osteoporosis.

SUMMARY OF THE INVENTION

This invention is based, at least in part, on the unexpected discovery that small molecule compounds described below can bind integrin and thus be used for diagnosing and treating various diseases and conditions.

Accordingly, in one aspect, the invention features a composition comprising a compound, or a pharmaceutically or cosmeceutically acceptable salt, solvate, or hydrate thereof, wherein the compound comprises one H-bond donor (HBD), one H-bond acceptor (HBA), two hydrophobic aromatic groups (HAR1 and HAR2), and one negatively ionizable group (NI), and wherein the compound is not compound A, B, or C,

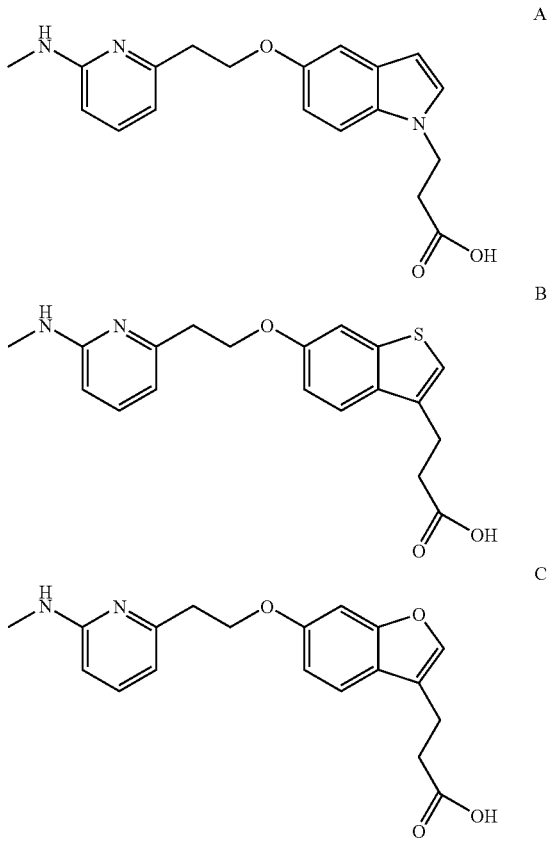

The composition may further comprises a pharmaceutically or cosmeceutically acceptable carrier.

In one embodiment, the HBD, HBA, HAR1, HAR2, and NI are configured according to FIG. 8A, wherein the distance between the HBD and the HRA1 is 2.81±1 Å, the distance between the HBD and the HBA is 7.52±1 Å, the distance between the HBD and the NI is 17.67±1 Å, the distance between the HRA1 and the HBA is 7.52±1 Å, the distance between the HRA1 and the HRA2 is 9.41±1 Å, the distance between the HBA and the NI is 10.20±1 Å, and the distance between the HRA2 and the NI is 5.88±1 Å. In particular, the distance between the HBD and the HRA1 may be 2.81 Å, the distance between the HBD and the HBA may be 7.52 Å, the distance between the HBD and the NI may be 17.67 Å, the distance between the HRA1 and the HBA may be 7.52 Å, the distance between the HRA1 and the HRA2 may be 9.41 Å, the distance between the HBA and the NI may be 10.20 Å, and the distance between the HRA2 and the NI may be 5.88 Å.

In another embodiment, the HBD, HBA, HAR1, HAR2, and NI are configured according to FIG. 8B, wherein the distance between the HBD and the HRA1 is 2.80±1 Å, the distance between the HBD and the HBA is 7.34±1 Å, the distance between the HBD and the NI is 16.92±1 Å, the distance between the HRA1 and the HBA is 5.20±1 Å, the distance between the HRA1 and the NI is 14.34±1 Å, the distance between the HBA and the HRA2 is 4.69±1 Å, the distance between the HBA and the NI is 9.85±1 Å, and the distance between the HRA2 and the NI is 5.66±1 Å. In particular, the distance between the HBD and the HRA1 may be 2.80 Å, the distance between the HBD and the HBA may be 7.34 Å, the distance between the HBD and the NI may be 16.92 Å, the distance between the HRA1 and the HBA may be 5.20 Å, the distance between the HRA1 and the NI may be 14.34 Å, the distance between the HBA and the HRA2 may be 4.69 Å, the distance between the HBA and the NI may be 9.85 Å, and the distance between the HRA2 and the NI may be 5.66 Å.

In still another embodiment, the HBD, HBA, HAR1, HAR2, and NI are configured according to FIG. 8C, wherein the distance between the HBD and the HRA1 is 2.79±1 Å, the distance between the HBD and the HRA2 is 11.94±1 Å, the distance between the HBD and the NI is 16.28±1 Å, the distance between the HRA1 and the HBA is 5.20±1 Å, the distance between the HRA1 and the NI is 14.64±1 Å, the distance between the HBA and the HRA2 is 4.72±1 Å, and the distance between the HRA2 and the NI is 5.63±1 Å. In particular, the distance between the HBD and the HRA1 may be 2.79 Å, the distance between the HBD and the HRA2 may be 11.94 Å, the distance between the HBD and the NI may be 16.28 Å, the distance between the HRA1 and the HBA may be 5.20 Å, the distance between the HRA1 and the NI may be 14.64 Å, the distance between the HBA and the HRA2 may be 4.72 Å, and the distance between the HRA2 and the NI may be 5.63 Å.

For example, a compound of the invention may be of Formula I, II, III, or IV:

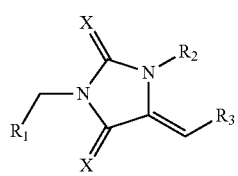

Formula I

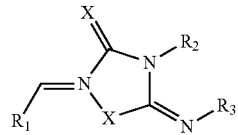

Formula II

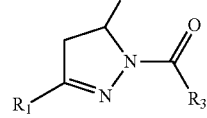

Formula III

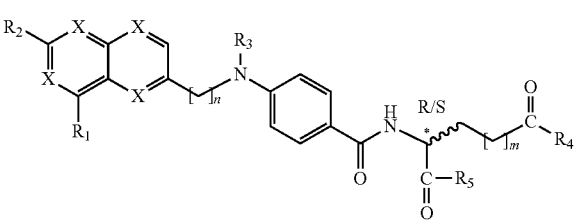

Formula IV

In Formulas I, II, and III, each of $R_1$ and $R_3$ is an aliphatic, aromatic, or heterocyclic group; $R_2$ is a substitution; and X is N, O, or S. In Formula IV, each of $R_1$ and $R_2$ is a hydrogen or halogen, a hydroxyl, sulfhydryl, alkoxy, aryloxy, carboxyl, nitro, cyano, amino, amido, or sulfonyl group, or any other organic functional group containing any number of carbon atoms; $R_3$ is a hydrogen, a hydroxyl, alkoxy, aryloxy, aromatic, or heterocyclic group, or an aliphatic chain of any number of carbon atoms; each of $R_4$ and $R_5$ is a hydroxyl or amino group; X is C, N, O, or S; m is a 0 to 3 atom linker group with carbon, nitrogen, oxygen, or sulfur atoms; and n is a 0 to 5 atom linker group with carbon, nitrogen, oxygen, or sulfur atoms.

In particular, in Formulas I, II, and III, each of $R_1$ and $R_3$ may be an alkyl, substituted alkyl, alkenyl, substituted alkenyl, alkynyl, substituted alkynyl, phenyl, substituted phenyl, aryl, substituted aryl, heteroaryl, or substituted heteroaryl group; $R_2$ may be a hydrogen or halogen, a hydroxyl, sulfhydryl, alkoxy, carboxyl, nitro, cyano, amino, amido, or sulfonyl group, or any other organic functional group containing any number of carbon atoms, or a combination thereof. The substituted alkyl, alkenyl, alkynyl, phenyl, aryl, or heteroaryl group in $R_1$ or $R_3$ may be an alkyl, alkenyl, alkynyl, phenyl, aryl, or heteroaryl group substituted by a halo, hydroxyl, sulfhydryl, alkoxy, carboxyl, carbonyl, nitro, cyano, amino, amido, sulfonyl, or substituted heterocyclic group. In Formula IV, the amino group in $R_4$ or $R_5$ may be substituted with an aliphatic, aromatic, or heterocyclic group. Examples of an compound of the invention include AV1-11, AV14-15, AV17-32, and AV34-38.

In another aspect, the invention features a composition comprising, or consisting of, a first compound (i.e., a compound of the invention as described above), or a pharmaceutically or cosmeceutically acceptable salt, solvate, or hydrate thereof, and one or more second compounds, wherein the second compounds are therapeutic agents, imaging agents, or a combination thereof.

For example, the second compounds may be vascular growth inhibitors (e.g., TNF-alpha, Angiostatin, Bevacizumab, Arresten, Canstatin, Combretastatin, Endostatin, NM-3, Thalidomide, Thrombospondin, Tumstatin, 2-methoxyestradiol, and Vitaxin), therapeutic agents for treating rheumatoid arthritis, radiotherapy agents, chemotherapy agents (e.g., cisplatin, doxorubicin, vincristine, cyclophosphamide, topotecan, paclitaxel, and other chemotherapeutic agents), therapeutic agents for treating bone metastases, therapeutic agents for treating osteoporosis (e.g., Fosemax, Aredia, Actonel, Dindronel, Cometa, Premarin, Climara, Estrae, Vivelle, Estraderm, Prempro, Premphase, Femhrt, Prefest, Combipatch, Evista, Calcitonin, Miacalcin, and Calcitonin), therapeutic agents for treating restenosis, vascular imaging agents (e.g., radionuclides), or a combination thereof.

In some embodiments, the first compound is operably linked to at least one of the second compounds.

The invention further provides a method of binding an integrin to a compound, comprising contacting an integrin with a compound of the invention, or a pharmaceutically or cosmeceutically acceptable salt, solvate, or hydrate thereof.

In one embodiment, the integrin is $\alpha_v\beta_3$. In another embodiment, the integrin is on a cell, for example, a cancer cell, a benign tumor cell, a stromal cell, a cell responding to, mediating, or regulating inflammation (e.g., a leukocyte, a macrophage, and a dendritic cell), a cell of the immune system (e.g., a leukocyte, a macrophage, and a dendritic cell), a cell involved in vascular functions (e.g., an endothelial cell, a cell related to an endothelial cell, and a smooth muscle cell), an osteoblast, an osteoclast, or a cell infected by a virus (e.g., Adenovirus (Adenoviridae), Coxackievirus (Picornaviridae), Echovirus (Picornaviridae), foot and mouth disease virus (Picornaviridae), Hantavirus (Buriyaviridae), human parechovirus (Picornaviridae), human immunodeficiency virus 1 (Retroviridae), and Rotavirus (Reoviridae)).

The method may further comprise contacting the cell with one or more therapeutic agents, imaging agents, or a combination thereof. The therapeutic and imaging agents are described above. The integrin and the cell may be contacted simultaneously or sequentially. The compound may be admixed with, or operably linked to, at least one of the agents.

Also within the invention is a method of binding an integrin to a compound in a subject, comprising administering to a subject in need thereof an effective amount of a compound of the invention, or a pharmaceutically or cosmeceutically acceptable salt, solvate, or hydrate thereof. The integrin may be $\alpha_v\beta_3$, and the subject may be an animal or a human being.

In one embodiment, the subject is suffering from or at risk for developing a cancer, e.g., a histological type of malignant solid tumor such as sarcoma or carcinoma, or a hematological malignancy associated with elevated levels of angiogenesis and angiogenic factors such as acute or chronic leukemia, multiple myeloma, myeloproliferative disease, non-Hodgkin's lymphoma, or Hodgkin's disease.

In another embodiment, the subject is suffering from or at risk for developing a benign tumor, e.g., a benign tumor or preneoplastic condition associated with increased vasularization, verruca vulgaris, pyogenic granuloma, rosacea, keloid scar, or an ocular tumor associated with choroidal or iris neovascularisation.

In yet another embodiment, the subject is suffering from or at risk for developing an inflammatory disease, e.g., an inflammatory bowel disease such as Crohn's disease or ulcerative colitis; an idiopathic inflammatory myopathy such as polymyositis (PM), dermatomyositis (DM), or related condition with increased vascularisation; another eye inflammatory disease; a disease or condition associated with increased inflammation such as gingivitis or mucositis; acne; or an gastrointestinal disease especially associated with chronic inflammatory conditions such as gastritis or duodenitis. An example of the mucositis is radiation- or chemotherapy-induced mucositis.

In yet another embodiment, the subject is suffering from or at risk for developing an immune or autoimmune disease, e.g., rheumatoid arthritis; psoriatic arthritis; psoriasis; multiple sclerosis; asthma bronchiale or allergy; eczema or dermatitis; or another inflammatory condition of skin or subcutaneous tissue such as erythematosquamous dermatosis, parakeratosis variegate, seborrheic dermatitis, seborrhea capitis, other seborrheic dermatitis, atopic dermatitis or related condition, erythema, Besnier's prurigo, neurodermatitis, contact dermatitis or other eczema, bullous dermatose, erythematous condition, lichen, pruritus or related condition, dermatitis herpetiformis, dermatosis herpetiformis, Duhring's disease, dermatitis herpetiformis, subcorneal pustular dermatosis, Sneddon-Wilkinson disease, juvenile dermatitis herpetiformis, juvenile pemphigoid, impetigo herpetiformis, erythema multiforme, erythema iris, herpes iris, Lyell's syndrome, lupus erythematosus, other specified erythematous condition, lichenification or lichen simplex chronicus, or Hyde's disease. Examples of the contact dermatitis and other eczema include dermatitis due to substances taken internally, dermatitis due to chemical products, drugs, and medicines in contact with skin, dermatitis due to solar radiation, sunburn, berloque dermatitis, photoallergic response dermatitis, phototoxic response dermatitis, polymorphous light eruption, disseminated superficial actinic porokeratosis (DSAP), dermatitis due to cosmetics, dermatitis due to infrared rays, dermatitis due to ultraviolet rays, and dermatitis due to treatment with ionizing radiation. Examples of the other specified erythematous condition include Ritter's disease, dermatitis exfoliativa neonatorum, and erythema intertrigo.

In yet another embodiment, the subject is suffering from or at risk for developing an vascular disease, e.g., endometriosis; dysfunctional uterine bleeding; endometrial hyperplasia; myelofibrosis; hemangioma; arteriosclerosis; acute or chronic transplant rejection or transplant vasculopathy; an ocular disorder characterized by ocular neovascularisation such as age-related macular degeneration (AMD), proliferative diabetic retinopathy (PDR), retinopathy of prematurity (ROP), neovascular glaucoma, retinoblastoma, retrolental fibroplasia, rubeosis, uveitis, macular degeneration, or corneal graft neovascularisation; a condition mediated by inappropriate platelet activation, recruitment, aggregation, or thrombosis such as coronary artery disease or injury, myocardial infarction or injury following myocardial infarction, stroke, unstable angina, preeclampsia, embolism, platelet-associated ischemic disorder, restenosis following percutaneous coronary intervention, thrombotic disorder, reocclusion following thrombosis, deep venous thrombosis (DVT), pulmonary embolism (PE), transient ischemic attack (TIA), or other condition where vascular occlusion is a common underlying feature; myocardial angiogenesis; a hemophilic joint; vascular adhesion; sepsis; adult respirator distress syndrome; telangiectasia; or wound granulation. Examples of the platelet-associated ischemic disorder include lung ischemia, coronary ischemia, and cerebral ischemia. Examples of the percutaneous coronary intervention include angioplasty, atherectomy, stent placement, and bypass surgery. Examples of the thrombotic disorder include coronary artery thrombosis, cerebral artery thrombosis, intracardiac thrombosis, peripheral artery thrombosis, venous thrombosis, and thrombosis and coagulopathies associated with exposure to a foreign or injured tissue surface.

In yet another embodiment, the subject is suffering from or at risk for developing a disease primarily associated with pathological bone resorption, e.g., steoporosis, Paget's disease of bone, or systemic parathormone (PTHrP)-mediated hypercalcemia.

In yet another embodiment, the subject is suffering from or at risk for developing a viral infection, e.g., an infection by Adenovirus (Adenoviridae), Coxackievirus (Picornaviridae), Echovirus (Picornaviridae), foot and mouth disease virus (Picornaviridae), Hantavirus (Buriyaviridae), human parechovirus (Picornaviridae), human immunodeficiency virus 1 (Retroviridae), or Rotavirus (Reoviridae).

The method may further comprise administering to the subject an effective amount of one or more therapeutic agents, imaging agents, or a combination thereof. The therapeutic and imaging agents are described above. The compound and the agents may be administered simultaneously or sequentially. The compound may be admixed with, or operably linked to, at least one of the agents.

A compound, therapeutic agent, imaging agent, or a combination thereof, may be administered parenterally, intradermally, subcutaneously, orally, transdermally, transmucosally, or rectally.

In some embodiments, the subject may be treated with angioplasty procedures (e.g., balloon angioplasty; laser angioplasty; coronary atherectomy or similar techniques; carotid endarterectomy; anastomosis of vascular grafts; surgery having a high risk of thrombus formation such as coronary bypass surgery and insertion of a prosthetic valve or vessel; atherectomy; stent placement; placement of a chronic cardiovascular device such as an in-dwelling catheter, prosthetic valve, or vessel; organ transplantation; and bypass surgery), radiotherapy, or chemotherapy (e.g., chemotherapy that involves administering to the subject an effective amount of cisplatin, doxorubicin, vincristine, cyclophosphamide, topotecan, paclitaxel, or other chemotherapeutic agents).

The invention additionally provides a computer-readable medium comprising a representation of a pharmacophore, wherein the pharmacophore includes features of one H-bond donor (HBD), one H-bond acceptor (HBA), two hydrophobic aromatic groups (HAR1 and HAR2), and one negatively ionizable group (NI).

In one embodiment, the HBD, HBA, HAR1, HAR2, and NI are configured according to FIG. 8A, wherein the distance between the HBD and the HRA1 is 2.81±1 Å, the distance between the HBD and the HBA is 7.52±1 Å, the distance between the HBD and the NI is 17.67±1 Å, the distance between the HRA1 and the HBA is 7.52±1 Å, the distance between the HRA1 and the HRA2 is 9.41±1 Å, the distance between the HBA and the NI is 10.20±1 Å, and the distance between the HRA2 and the NI is 5.88±1 Å. In particular, the distance between the HBD and the HRA1 may be 2.81 Å, the distance between the HBD and the HBA may be 7.52 Å, the distance between the HBD and the NI may be 17.67 Å, the distance between the HRA1 and the HBA may be 7.52 Å, the distance between the HRA1 and the HRA2 may be 9.41 Å, the distance between the HBA and the NI may be 10.20 Å, and the distance between the HRA2 and the NI may be 5.88 Å.

In another embodiment, the HBD, HBA, HAR1, HAR2, and NI are configured according to FIG. 8B, wherein the distance between the HBD and the HRA1 is 2.80±1 Å, the distance between the HBD and the HBA is 7.34±1 Å, the distance between the HBD and the NI is 16.92±1 Å, the distance between the HRA1 and the HBA is 5.20±1 Å, the distance between the HRA1 and the NI is 14.34±1 Å, the distance between the HBA and the HRA2 is 4.69±1 Å, the distance between the HBA and the NI is 9.85±1 Å, and the distance between the HRA2 and the NI is 5.66±1 Å. In particular, the distance between the HBD and the HRA1 may be 2.80 Å, the distance between the HBD and the HBA may be 7.34 Å, the distance between the HBD and the NI may be 16.92 Å, the distance between the HRA1 and the HBA may be 5.20 Å, the distance between the HRA1 and the NI may be 14.34 Å, the distance between the HBA and the HRA2 may be 4.69 Å, the distance between the HBA and the NI may be 9.85 Å, and the distance between the HRA2 and the NI may be 5.66 Å.

In still another embodiment, the HBD, HBA, HAR1, HAR2, and NI are configured according to FIG. 8C, wherein the distance between the HBD and the HRA1 is 2.79±1 Å, the distance between the HBD and the HRA2 is 11.94±1 Å, the distance between the HBD and the NI is 16.28±1 Å, the distance between the HRA1 and the HBA is 5.20±1 Å, the distance between the HRA1 and the NI is 14.64±1 Å, the distance between the HBA and the HRA2 is 4.72±1 Å, and the distance between the HRA2 and the NI is 5.63±1 Å. In particular, the distance between the HBD and the HRA1 may be 2.79 Å, the distance between the HBD and the HRA2 may be 11.94 Å, the distance between the HBD and the NI may be 16.28 Å, the distance between the HRA1 and the HBA may be 5.20 Å, the distance between the HRA1 and the NI may be 14.64 Å, the distance between the HBA and the HRA2 may be 4.72 Å, and the distance between the HRA2 and the NI may be 5.63 Å.

Another feature of the invention is a method of identifying an integrin-binding small molecule. The method comprises comparing the three-dimensional structure of a compound with the three-dimensional structure of a pharmacophore described above, and selecting the compound if the compound conforms to the features of the pharmacophore.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Integrin $\alpha_v\beta_3$ has been implicated in multiple aspects of tumor progression, metastasis, and osteoclast bone resorption. Many tumors have high expression of $\alpha_v\beta_3$, and this expression correlates with tumor progression in melanoma, glioma, ovarian, prostate, breast cancer, as well as other cancers. The $\alpha_v\beta_3$ receptor is being evaluated as a therapeutic target for novel anticancer agents. We have discovered a series of structurally diverse small-molecule $\alpha_v\beta_3$ antagonists utilizing chemical function-based common feature pharmacophore models. The three-dimensional (3D) pharmacophore models were generated using a training set of three recently reported $\alpha_v\beta_3$ receptor antagonists. Upon validation using a database of known antagonists of $\alpha_v\beta_3$ receptor, the pharmacophore model with high discriminative ability was used as a 3D query to retrieve compounds with novel structural scaffolds and desired chemical features. A search of a database of approximately 600,000 compounds using Hypo5 yielded 832 compounds. On the basis of structural novelty, calculated physicochemical properties and sample availability, 38 compounds were selected to screen in a $\alpha_v\beta_3$ receptor-binding assay. Of the 29 compounds tested in $\alpha_v\beta_3$ receptor specific binding assay, four compounds showed nanomolar binding affinity. A limited structure-activity relationship analysis on one of the active compounds (AV26) resulted in discovery of two potent non-RGD mimetic antagonists with nanomolar to subnanomolar binding affinity. All the active compounds evaluated in a panel of cancer cell lines showed no cytotoxicity at low micromolar concentrations except AV26, which showed considerable cytotoxicity in a breast cancer cell line. Our novel small-molecule compounds could be conjugated to anticancer drugs such as paclitaxel for selective delivery to $\alpha_v\beta_3$ positive metastatic cancers.

Compositions

Accordingly, the invention provides a composition comprising a compound, or a pharmaceutically or cosmeceutically acceptable salt, solvate, or hydrate thereof, wherein the compound comprises one H-bond donor (HBD), one H-bond acceptor (HBA), two hydrophobic aromatic groups (HAR1 and HAR2), and one negatively ionizable group (NI), and wherein the compound is not compound A, B, or C.

The composition may further comprise a pharmaceutically or cosmeceutically acceptable carrier. "Pharmaceutically or cosmeceutically acceptable carriers" include solvents, dispersion media, coatings, antibacterial and antifungal agents, isotonic and absorption delaying agents, and the like, compatible with pharmaceutical or cosmeceutical administration.

Figure 8:
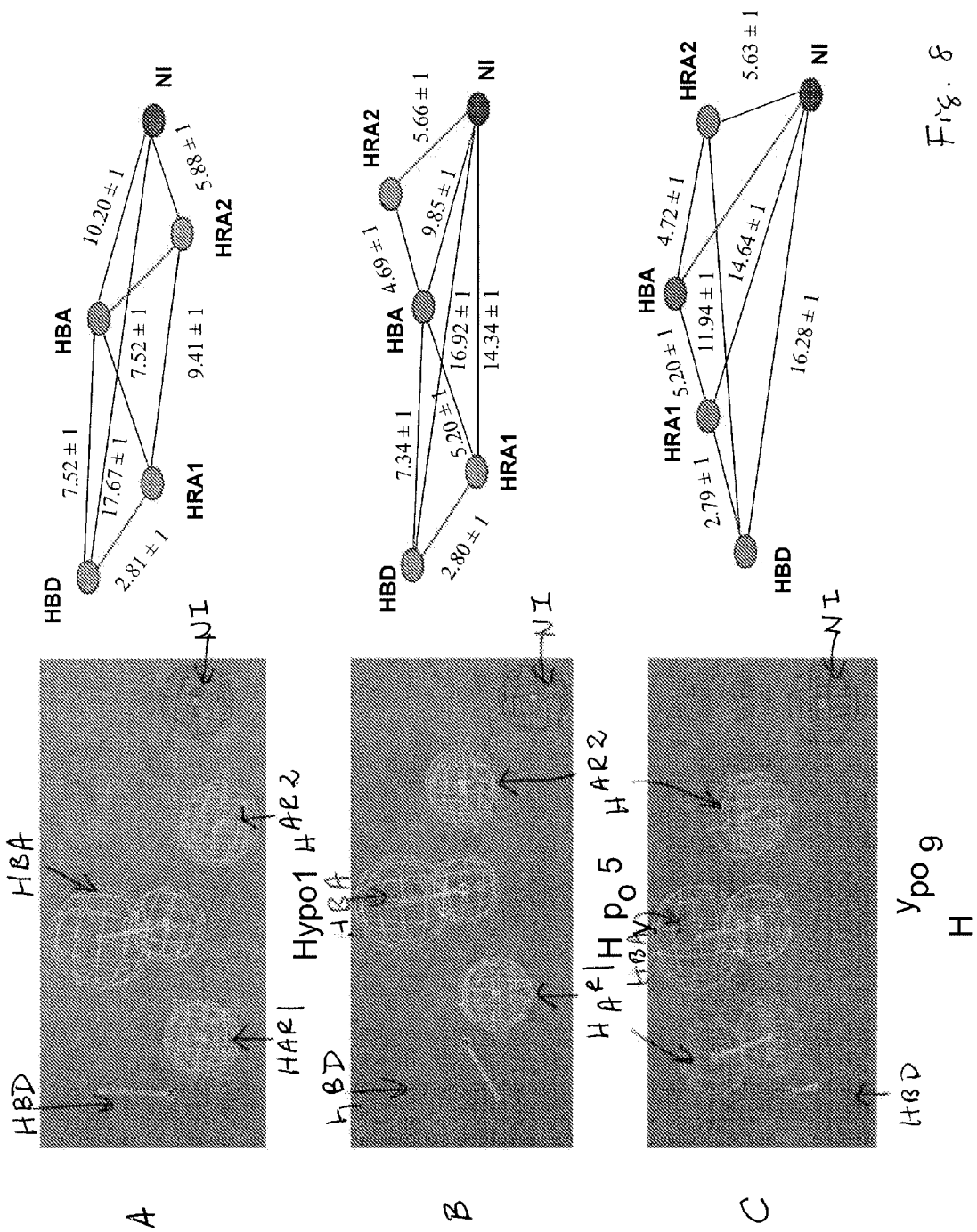
FIG. 8 depicts the common feature pharmacophore Hypos 1 (A), 5 (B), and 9 (C). The pharmacophore features are shown as H-bond donor (HBD) in magenta, H-bond acceptor (HBA) in green, hydrophobic aromatic (HAR1-HAR2) in brown, and negatively ionizable feature (NI) in blue. The inter-feature distances are given in Å.

In one embodiment, the HBD, HBA, HAR1, HAR2, and NI are configured according to FIG. 8A, wherein the distance between the HBD and the HRA1 is 2.81±1 Å, the distance between the HBD and the HBA is 7.52±1 Å, the distance between the HBD and the NI is 17.67±1 Å, the distance between the HRA1 and the HBA is 7.52±1 Å, the distance between the HRA1 and the HRA2 is 9.41±1 Å, the distance between the HBA and the NI is 10.20±1 Å, and the distance between the HRA2 and the NI is 5.88±1 Å. In particular, the distance between the HBD and the HRA1 may be 2.81 Å, the distance between the HBD and the HBA may be 7.52 Å, the distance between the HBD and the NI may be 17.67 Å, the distance between the HRA1 and the HBA may be 7.52 Å, the distance between the HRA1 and the HRA2 may be 9.41 Å, the distance between the HBA and the NI may be 10.20 Å, and the distance between the HRA2 and the NI may be 5.88 Å.

In another embodiment, the HBD, HBA, HAR1, HAR2, and NI are configured according to FIG. 8B, wherein the distance between the HBD and the HRA1 is 2.80±1 Å, the distance between the HBD and the HBA is 7.34±1 Å, the distance between the HBD and the NI is 16.92±1 Å, the distance between the HRA1 and the HBA is 5.20±1 Å, the distance between the HRA1 and the NI is 14.34±1 Å, the distance between the HBA and the HRA2 is 4.69±1 Å, the distance between the HBA and the NI is 9.85±1 Å, and the distance between the HRA2 and the NI is 5.66±1 Å. In particular, the distance between the HBD and the HRA1 may be 2.80 Å, the distance between the HBD and the HBA may be 7.34 Å, the distance between the HBD and the NI may be 16.92 Å, the distance between the HRA1 and the HBA may be 5.20 Å, the distance between the HRA1 and the NI may be 14.34 Å, the distance between the HBA and the HRA2 may be 4.69 Å, the distance between the HBA and the NI may be 9.85 Å, and the distance between the HRA2 and the NI may be 5.66 Å.

In still another embodiment, the HBD, HBA, HAR1, HAR2, and NI are configured according to FIG. 8C, wherein the distance between the HBD and the HRA1 is 2.79±1 Å, the distance between the HBD and the HRA2 is 11.94±1 Å, the distance between the HBD and the NI is 16.28±1 Å, the distance between the HRA1 and the HBA is 5.20±1 Å, the distance between the HRA1 and the NI is 14.64±1 Å, the distance between the HBA and the HRA2 is 4.72±1 Å, and the distance between the HRA2 and the NI is 5.63±1 Å. In particular, the distance between the HBD and the HRA1 may be 2.79 Å, the distance between the HBD and the HRA2 may be 11.94 Å, the distance between the HBD and the NI may be 16.28 Å, the distance between the HRA1 and the HBA may be 5.20 Å, the distance between the HRA1 and the NI may be 14.64 Å, the distance between the HBA and the HRA2 may be 4.72 Å, and the distance between the HRA2 and the NI may be 5.63 Å.

A compound of the invention may be of Formula I, II, III, or IV.

In Formulas I, II, and III, each of $R_1$ and $R_3$ is an aliphatic, aromatic, or heterocyclic group; $R_2$ is a substitution; and X is N, O, or S. In some embodiments, each of $R_1$ and $R_3$ is an alkyl, substituted alkyl, alkenyl, substituted alkenyl, alkynyl, substituted alkynyl, phenyl, substituted phenyl, aryl, substituted aryl, heteroaryl, or substituted heteroaryl group; $R_2$ is a hydrogen or halogen, a hydroxyl, sulfhydryl, alkoxy, carboxyl, nitro, cyano, amino, amido, or sulfonyl group, or any other organic functional group containing any number of carbon atoms; or a combination there of. In other embodiments, the substituted alkyl, alkenyl, alkynyl, phenyl, aryl, or heteroaryl group in $R_1$ or $R_3$ is an alkyl, alkenyl, alkynyl, phenyl, aryl, or heteroaryl group substituted by a halo, hydroxyl, sulfhydryl, alkoxy, carboxyl, carbonyl, nitro, cyano, amino, amido, sulfonyl, or substituted heterocyclic group.

In Formula IV, each of $R_1$ and $R_2$ is a hydrogen or halogen, a hydroxyl, sulfhydryl, alkoxy, aryloxy, carboxyl, nitro, cyano, amino, amido, or sulfonyl group, or any other organic functional group containing any number of carbon atoms; $R_3$ is a hydrogen, a hydroxyl, alkoxy, aryloxy, aromatic, or heterocyclic group, or an aliphatic chain of any number of carbon atoms; each of $R_4$ and $R_5$ is a hydroxyl or amino group; X is C, N, O, or S; m is a 0 to 3 atom linker group with carbon, nitrogen, oxygen, or sulfur atoms; and n is a 0 to 5 atom linker group with carbon, nitrogen, oxygen, or sulfur atoms. In some embodiments, the amino group in $R_4$ or $R_5$ is substituted with an aliphatic, aromatic, or heterocyclic group.

Examples of a compound of the invention include AV1-11, AV14-15, AV17-32, and AV34-38.

A compound of the invention may be obtained by chemical synthesis using methods well known in the art, or from commercial sources. The composition of the invention is useful for diagnosing and treating diseases described below.

In some embodiments, a compound of the invention may be used in combination with one or more therapeutic agents, imaging agents, or a combination thereof. The therapeutic agents include, but are not limited to, any small molecule drug, antibody, FC-fragment, protein-based drug, oligonucleotide, siRNA, aptamer, or ankyrin repeat. Particular examples of the therapeutic agents include vascular growth inhibitors (e.g., TNF-alpha, Angiostatin, Bevacizumab, Arresten, Canstatin, Combretastatin, Endostatin, NM-3, Thalidomide, Thrombospondin, Tumstatin, 2-methoxyestradiol, and Vitaxin), therapeutic agents for treating rheumatoid arthritis, radiotherapy agents, chemotherapy agents (e.g., cisplatin, doxorubicin, vincristine, cyclophosphamide, topotecan, paclitaxel, and other chemotherapeutic agents), therapeutic agents for treating bone metastases, therapeutic agents for treating osteoporosis (e.g., Fosemax, Aredia, Actonel, Dindronel, Cometa, Premarin, Climara, Estrae, Vivelle, Estraderm, Prempro, Premphase, Femhrt, Prefest, Combipatch, Evista, Calcitonin, Miacalcin, and Calcitonin), and therapeutic agents for treating restenosis. The imaging agents include, but are not limited to, radionuclides (i.e., radioactive metal ions that produce imageable gamma ray or positron emissions).

The compound of the invention may be operably linked to at least one of the therapeutic or imaging compounds to form a conjugate. By "operably linked" is meant that the compound of the invention and the therapeutic or imaging agent are connected such that the binding of the compound to an integrin on a cell and the function of the therapeutic or imaging agent are not disturbed.

Most cancer chemotherapeutics that are widely in use at present, including but not limited to cisplatin, doxorubicin, vincristine, cyclophosphamide, topotecan, and paclitaxel, possess little selectivity for cancer cells. The same problem arises with many treatments used for non-cancer indications such as rheumatoid arthritis, where side effects, especially after prolonged treatment courses may occur. In many cases this leads to unwanted side effects and increased toxicities against normal tissues. As a result of toxicities to normal tissues, many anticancer chemotherapeutics as well as non-cancer medicaments are often given at suboptimal doses, or the treatment has to be interrupted, resulting in reduced efficacy and the eventual failure of therapy. This may be accompanied by the development of drug resistance. A widely cited example of this is the dose-limiting cardiotoxicity of therapy with anthracyclines. The selective toxicity of a given drug can be increased by either increasing the dose of the drug that reaches the diseased tissue or by decreasing the dose that reaches normal tissues, or both.

Delivery of drugs to target cells can be selectively increased by associating the drugs with molecules that bind to antigens or receptors that are either uniquely expressed or overexpressed on the target cells relative to normal tissues. This allows specific delivery of drugs to the target cells. For example, since $\alpha_v\beta_3$ integrins are known to be overexpressed on the neovasculature of tumors and during inflammatory diseases, as well as on osteoclasts, a conjugate of the invention can be used to selectively target these cells.

A conjugate of the invention may be constructed using any of the methods well known in the art. Detailed descriptions of these methods can be found, e.g., in "Bioconjugate Techniques" by G. T. Hermanson, Academic Press, San Diego, 1996, the content of which is incorporated herein by reference in its entirety.

For example, conjugation of a compound of the invention to other molecules of interest (e.g., antibodies, medicaments, DNA and siRNA molecules, lipids, etc.) may be most easily performed by chemical crosslinking using commonly available and published technologies. Crosslinking is the process of chemically joining two or more molecules by a covalent bond. Crosslinking reagents contain reactive ends to specific functional groups (e.g., primary amines, sulfhydryls, etc.) on proteins or other molecules. Because of the availability of several chemical groups in proteins and peptides that may be targets for reactions, proteins and peptides are readily conjugated and otherwise studied using crosslinking methods. Crosslinkers also are commonly used to modify nucleic acids, drugs, and solid surfaces. They also are useful for preparing antibody-enzyme conjugates, immunotoxins, and other labeled protein reagents. By derivatizing a receptor with a crosslinker before or after contact with the ligand (e.g., a compound of the invention), it is possible to isolate the receptor-ligand complex. The use of radioiodinatable crosslinkers makes it possible to identify a particular receptor by autoradiographic detection. Crosslinkers are selected on the basis of their chemical reactivities (i.e., specificity for particular functional groups) and compatibility of the reaction with the application. The best crosslinker to use for a specific application must be determined empirically. Crosslinkers are chosen based on the following characteristics: chemical specificity, spacer arm length, water solubility and cell membrane permeability, same (homobifunctional) or different (heterobifunctional) reactive groups, spontaneously reactive or photoreactive groups, and cleavability. Crosslinkers contain at least two reactive groups. Functional groups that can be targeted for crosslinking include primary amines, sulfhydryls, carbonyls, carbohydrates, and carboxylic acids (Table A). Coupling also can be nonselective using a photoreactive phenyl azide crosslinker.

TABLE A

Examples of reactive crosslinker groups and their functional group targets.

| Reactive Group | Target Functional Group |
| --- | --- |
| Aryl azide | Nonselective (or primary amine) |
| Carbodiimide | Amine/Carboxyl |
| Hydrazide | Carbohydrate (oxidized) |
| Hydroxymethyl phosphine | Amine |
| Imidoester | Amine |
| Isocyanate | Hydroxyl (non-aqueous) |
| Carbonyl | Hydrazine |
| Maleimide | Sulfhydryl |
| NHS-ester | Amine |
| PFP-ester | Amine |
| Psoralen | Thymine (photoreactive intercalator) |
| Pyridyl disulfide | Sulfhydryl |
| Vinyl sulfone | Sulfhydryl, amine, hydroxyl |
| Carbonyl | Hydrazine |

Often different spacer arm lengths are required because steric effects dictate the distance between potential reaction sites for crosslinking. Usually, a crosslinker with a short (4-8 Å) spacer arm is used first and the degree of crosslinking determined. A crosslinker with a longer spacer arm may then be used to optimize crosslinking efficiency. Short spacer arms are often used in intramolecular crosslinking studies, and intermolecular crosslinking is favored with a crosslinker containing a long spacer arm. In many applications, it is necessary to maintain the native structure of a protein, so crosslinking is most often performed using mild pH and buffer conditions. Furthermore, optimal crosslinker-to-protein molar ratios for reactions must be determined. Depending on the application, the degree of conjugation is an important factor. For example, when preparing immunogen conjugates, a high degree of conjugation is desired to increase the immunogenicity of the antigen. However, when conjugating to an antibody or an enzyme, a low- to moderate-degree of conjugation may be optimal so that biological activity of the protein is retained. The number of functional groups on the protein's surface is also important to consider. If there are numerous target groups, a lower crosslinker-to-protein ratio can be used. For a limited number of potential targets, a higher crosslinker-to-protein ratio may be required. Furthermore, the number of components should be kept to a minimum because conjugates consisting of more than two components are difficult to analyze and provide less information on spatial arrangements of protein subunits. Water solubility and membrane permeability is also an important issue in choosing the optimal crosslinker for coupling. Many crosslinkers, by virtue of their hydrophobic spacer arms, have limited solubility in aqueous solutions. These crosslinkers are generally dissolved in DMF or DMSO, and then added to the biological system or solution of biomolecules to be crosslinked. Hydrophobic crosslinkers are able to cross cellular and organellar membranes and effect crosslinking both at the outer surface of a membrane and within the membrane-bounded space. It is often inconvenient or undesirable to introduce organic solvents into a crosslinking procedure for a biological system. It is also desirable in many instances to effect crosslinking only on the outer surface of a cellular or organellar membrane without altering the interior of the cell or organelle and, in such cases, several water-soluble, membrane-impermeable crosslinkers are available. Some crosslinkers contain a spacer arm formed from polyethylene glycol (PEG) subunits and resulting in a polyethylene oxide (PEO) chain with abundant oxygen atoms to provide water solubility. These crosslinkers are designated by a (PEO)n in their name and are both water-soluble and unable to penetrate biological membranes. They provide the added benefit of transferring their hydrophilic spacer to the crosslinked complex, thus decreasing the potential for aggregation and precipitation of the complex. Other crosslinkers obtain their water-solubility and membrane-impermeability by virtue of a charged reactive group at either end of the spacer. Charged reactive groups, such as sulfo-NHS esters or imidoesters, impart water-solubility to the crosslinking reagent, but not to the crosslinked complex because the reactive group is not a part of the final complex.

For illustration purposes, two examples are provided below for constructing NVX-188 (i.e., AV38) conjugates.

Example 1

Coupling of the Carboxyl Group of NVX-188 and Analogues by Using Carboyl-Reactive Chemistry Several members of the NVX-188 group contain carboxyl groups which can serve as coupling partners for various crosslinkers. Carbodiimides couple carboxyls to primary amines or hydrazides, resulting in the formation of amide or hydrazone bonds. Carbodiimides are unlike other conjugation reactions in that no spacer exists between the molecules being coupled. Carboxy termini of proteins can also be targeted, as well as glutamic and aspartic acid side chains. In this example, EDC (Product #22980, 22981, Pierce) reacts with carboxylic acid group and activates the carboxyl group to form an active O-acylisourea intermediate, allowing it to be coupled to the amino group in the reaction mixture. An EDC byproduct is released as a soluble urea derivative after displacement by the nucleophile. The O-acylisourea intermediate is unstable in aqueous solutions, making it ineffective in two-step conjugation procedures without increasing the stability of the intermediate using N-hydroxysuccinimide. This intermediate reacts with a primary amine to form an amide derivative. Failure to react with an amine results in hydrolysis of the intermediate, regeneration of the carboxyls, and the release of an N-unsubstituted urea. The crosslinking reaction is usually performed between pH 4.5 to 5 and requires only a few minutes for many applications. However, the yield of the reaction is similar at pH from 4.5 to 7.5. The hydrolysis of EDC is a competing reaction during coupling and is dependent on temperature, pH, and buffer composition. 4-Morpholinoethanesulfonic acid (MES, Product #28390, Pierce) is an effective carbodiimide reaction buffer. Phosphate buffers reduce the reaction efficiency of the EDC, but increasing the amount of EDC can compensate for the reduced efficiency. Tris, glycine, and acetate buffers may not be used as conjugation buffers. NHS (Product #24500, Pierce Biotechnology) or its water-soluble analog Sulfo-NHS (Product #24510, Pierce) is often included in EDC-coupling protocols to improve efficiency. EDC couples NHS to carboxyls, resulting in an NHS-activated site on a molecule. The NHS-ester formed and the carbodiimide's O-acylisourea intermediate are amine-reactive; however, an NHS-ester has much greater stability in slightly acidic or near-neutral pH conditions. In water, an NHS-ester has a half-life of one to several hours, or even days, depending on temperature, pH, and structure of the crosslinker, but O-acylisourea intermediate has a half-life measured in seconds in acidic or neutral pH conditions. EDC-mediated coupling of molecules works well in many applications without the addition of NHS or Sulfo-NHS, which are not generally required unless protein concentrations are very low. When a large excess of EDC is used without NHS, it is often necessary to reduce the EDC amount when converting to an EDC/NHS system to prevent excessive crosslinking and possible precipitation.

Example 2

Coupling of NVX-188 and Analogues Using Non-Specific Chemistries (Aryl Azides)

Photoreactive reagents are chemically inert reagents that become reactive when exposed to ultraviolet or visible light. With few exceptions, the photoreactive groups in these reagents are aryl azides. When an aryl azide is exposed to UV light, it forms a nitrene group that can initiate addition reactions with double bonds, insertion into C—H and N—H sites, or subsequent ring expansion to react with a nucleophile (e.g., primary amines). The latter reaction path dominates when primary amines are present in the sample. Thiol-containing reducing agents (e.g., DTT or 2-mercaptoethanol) must be avoided in the sample solution during all steps before and during photoactivation. These reagents will reduce the azide functional group to an amine, preventing photoactivation. Reactions can be performed in a variety of amine-free buffer conditions. If working with heterobifunctional photoreactive crosslinkers, buffers should be used compatible with the chemically reactive portion of the reagent. The chemical reaction is performed in subdued light with reaction vessels covered in foil. The photoactivation can be performed with a bright camera flash or ultraviolet hand-held lamp about one to two inches above the reaction vessels. A bright camera flash works well with the nitro- and hydroxyl-substituted aryl azides. Unsubstituted aryl azides may require ultraviolet light or numerous flashes.

A composition of the invention is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Compositions suitable for injectable use include sterile aqueous solutions (where water soluble) or dispersions and sterile powders for the extemporaneous preparation of sterile injectable solutions or dispersion. For intravenous administration, suitable carriers include physiological saline, sterile water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the compounds in the required amounts in an appropriate solvent with one or a combination of ingredients enumerated above, as required, followed by filtered sterilization. Generally, dispersions are prepared by incorporating the compounds into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the compounds can be incorporated with excipients and used in the form of tablets, troches, or capsules, e.g., gelatin capsules. Oral compositions can also be prepared using a fluid carrier for use as a mouthwash. Pharmaceutically or cosmeceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compositions are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The compositions of the invention can also be prepared in the form of suppositories (e.g., with conventional suppository bases such as cocoa butter and other glycerides) or retention enemas for rectal delivery.

In one embodiment, the compositions are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically or cosmeceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form," as used herein, refers to physically discrete units suited as unitary dosages for the subject to be treated; each unit containing a predetermined quantity of active compound calculated to produce the desired therapeutic or cosmeceutic effect in association with the required pharmaceutical or cosmeceutical carrier.

The compositions of the invention can be included in a container, pack, or dispenser together with instructions for administration to form packaged products. Other active compounds can also be incorporated into the compositions.

Uses of the Compositions
Methods of Treatment

One object of the invention is to provide a method for binding an integrin to a compound in vitro or in vivo, thereby modulating the activity of the integrin. The method comprises contacting an integrin with a compound of the invention, or a pharmaceutically or cosmeceutically acceptable salt, solvate, or hydrate thereof.

Integrins are a family of glycoproteins that form cell adhesion and signaling receptors. At least 25 integrin receptors, each formed by a heterodimer of an alpha and beta subunit, have been identified. $\alpha_v\beta_3$ integrin is a prominent member of the integrin family.

Integrins respond to cues from the extracellular matrix to modulate cellular responses, including cell death, proliferation, migration, and tissue remodeling. Signaling is mediated through recruitment of tyrosine kinases from the FAK and Src families. This modulates activity of the MAP kinase and PI3K transduction cascades. Lack of integrin-mediated adhesion to the extracellular matrix triggers apoptosis in endothelial cells. Many integrins bind specifically to an RGD tripeptide motif (Arg-Gly-Asp) that is found on many extracellular proteins.

The expression of $\alpha_v\beta_3$ is low in most tissues, but greatly increases in remodeling or growing tissues. $\alpha_v\beta_3$ binds to the RGD motif of the extracellular matrix proteins fibronectin, fibrinogen, osteopontin, thrombospondin, and vitronectin. It plays a key role in the proliferation and metastasis of tumors, bone resorption, certain inflammatory diseases, and blood vessel formation (angiogenesis). $\alpha_v\beta_3$ integrin's biological actions provide the basis for therapeutic and cosmeceutic interventions using selective $\alpha_v\beta_3$ antagonists in a range of indications. These indications include, but are not limited to, cancer, osteoporosis, rheumatoid arthritis, and age-related macular degeneration.

Accordingly, in one embodiment, a compound of the invention is contacted with an integrin on a cell, e.g., a cancer cell, a benign tumor cell, a stromal cell, a cell responding to, mediating, or regulating inflammation (e.g., a leukocyte, a macrophage, and a dendritic cell), a cell of the immune system (e.g., a leukocyte, a macrophage, and a dendritic cell), a cell involved in vascular functions (e.g., an endothelial cell, a cell related to an endothelial cell, and a smooth muscle cell), an osteoblast, an osteoclast, or a cell infected by a virus (e.g., Adenovirus (Adenoviridae), Coxackievirus (Picornaviridae), Echovirus (Picornaviridae), foot and mouth disease virus (Picornaviridae), Hantavirus (Buriyaviridae), human parechovirus (Picornaviridae), human immunodeficiency virus 1 (Retroviridae), and Rotavirus (Reoviridae)).

The invention further provides for both prophylactic and therapeutic or cosmeceutic methods of treating a subject in need thereof an effective amount of a compound described above.

"Subject," as used herein, refers to a human or animal, including all vertebrates, e.g., mammals, such as primates (particularly higher primates), sheep, dog, rodents (e.g., mouse or rat), guinea pig, goat, pig, cat, rabbit, cow; and non-mammals, such as chicken, amphibians, reptiles, etc. In a preferred embodiment, the subject is a human. In another embodiment, the subject is an animal.

A subject to be treated may be identified, e.g., using diagnostic methods known in the art, as being suffering from or at risk for developing a disease or condition described below. The subject may be identified in the judgment of a subject or a health care professional, and can be subjective (e.g., opinion) or objective (e.g., measurable by a test or diagnostic method).

As used herein, the term "treatment" is defined as the application or administration of a therapeutic or cosmeceutic agent to a subject, or application or administration of a therapeutic or cosmeceutic agent to an isolated tissue or cell line from a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease.

An "effective amount" is an amount of a therapeutic or cosmeceutic agent that is capable of producing a medically or cosmeceutically desirable result as delineated herein in a treated subject. The medically or cosmeceutically desirable result may be objective (i.e., measurable by some test or marker) or subjective (i.e., subject gives an indication of or feels an effect).

Toxicity and therapeutic or cosmeceutic efficacy of a compound of the invention can be determined by standard pharmaceutical or cosmeceutical procedures in cell cultures or experimental animals, e.g., for determining the $LD_{50}$ (the dose lethal to 50% of the population) and the $ED_{50}$ (the dose therapeutically or cosmeceutically effective in 50% of the population). The dose ratio between toxic and therapeutic or cosmeceutically effects is the therapeutic index, and can be expressed as the ratio $LD_{50}/ED_{50}$. Compounds which exhibit high therapeutic or cosmeceutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of the compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically or cosmeceutically effective dose can be estimated initially from cell culture assays. A dose may be formulated in animal models to achieve a circulating plasma concentration range that includes the $IC_{50}$ (i.e., the concentration of a compound which achieves a half-maximal inhibition of symptoms) as determined in cell culture. Such information can be used to more accurately determine useful doses in humans. Levels in plasma may be measured, for example, by high performance liquid chromatography.

A therapeutically or cosmeceutically effective amount of the compounds (i.e., an effective dosage) may range from, e.g., about 1 microgram per kilogram to about 500 milligrams per kilogram, about 100 micrograms per kilogram to about 5 milligrams per kilogram, or about 1 microgram per kilogram to about 50 micrograms per kilogram. The compounds can be administered, e.g., one time per week for between about 1 to 10 weeks, preferably between 2 to 8 weeks, more preferably between about 3 to 7 weeks, and even more preferably for about 4, 5, or 6 weeks. In subjects suffering from chronic diseases, such as arthritis or osteoporosis, life-long treatment may be necessary, for example, one time every day or preferably one time per week. It is furthermore understood that appropriate doses of a compound depend upon the potency of the compound. When one or more of these compounds is to be administered to a subject (e.g., an animal or a human), a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, the severity of the disease or disorder, previous treatments, and other diseases present. Moreover, treatment of a subject with a therapeutically or cosmeceutically effective amount of the compounds can include a single treatment or, preferably, can include a series of treatments.

The method of the invention has numerous applications. One example of the application is the treatment of cancer including, but not limited to, all histological types of malignant solid tumors such as sarcomas and carcinomas, and hematological malignancies associated with elevated levels of angiogenesis and angiogenic factors such as acute and chronic leukemias, multiple myeloma, myeloproliferative diseases, non-Hodgkin's lymphomas, and Hodgkin's disease.

Tumor Growth & Metastasis: $\alpha_v\beta_3$ integrin is expressed by many tumors, including malignant melanoma, breast cancer, ovarian cancer, and glioma and colon cancer. Over-expression in these tumors is associated with malignant progression, including invasion and metastasis. Experimental support for a potential role of $\alpha_v\beta_3$ integrin antagonists for cancer therapy includes:

1) reduction in liver meta-stases following injection of murine colon cancer cells in mice treated with an $\alpha_v\beta_3$ integrin antagonist, 2) induction of apoptosis in brain tumor cells in vitro following exposure to a cyclic RGD penta-peptide, 3) inhibition of growth of melanoma xenografts in mice by an oligopeptide $\alpha_v\beta_3$ integrin antagonist, 4) synergistic effects of radioimmunotherapy and Cilengitide (a cyclic RGD peptide) to increase tumor apoptosis and cure rate and of breast cancer xenografts in mice, 5) growth inhibition (and reduced angiogenesis) of breast cancer tumors in a human skin transplant in SCID mice by monoclonal antibodies to $\alpha_v\beta_3$ integrin, 6) correlation of expression of $\alpha_v\beta_3$ integrin with tumor progression in several tumor types, including melanoma, glioma, breast, and ovarian cancer, 7) increased metastatic potential of MDA-MB 435 breast cancer cells associated with a mutant (constitutively activated) variant of $\alpha_v\beta_3$ integrin, and 8) increased incidence of bone metastases from tumors transfected to express $\alpha_v\beta_3$ integrin at high levels, and suppression of bone metastases of MDA-MB 435 breast cancer xenografts in mice with treatment by an $\alpha_v\beta_3$ integrin antagonist.

Since $\alpha_v\beta_3$ integrin plays a key role in tumor cell invasion and tumor cell spread, $\alpha_v\beta_3$ integrin antagonists, particularly those able to block invading cancer cells from binding to extracellular matrix proteins, with a low toxicity profile, such as NVX-188, are of special interest for this application and also appear to be well suited for combinatorial treatment strategies.

Angiogenesis: $\alpha_v\beta_3$ integrin is expressed on vascular smooth muscle cells during neovascularization. A central role of $\alpha_v\beta_3$ integrin in blood vessel development has been demonstrated in experiments. In these experiments, new blood vessel growth (i.e., into tumors) was substantially blocked by $\alpha_v\beta_3$ integrin antagonists. Some of the $\alpha_v\beta_3$ integrin antagonist's therapeutic benefits in cancer derive not from directly killing tumors, but from inhibiting tumor vascularization. For example, it has been shown that lung metastases development by melanoma cells, in an animal model, could be prevented with an $\alpha_v\beta_3$ integrin antagonist. This occurred even though the melanoma cells did not express $\alpha_v\beta_3$ integrin. Thus, non-cytotoxic $\alpha_v\beta_3$ blockers have potential angiogenesis inhibiting applications in cancer therapy.

Targeted Therapy: NVX-188's high specificity for a key cell surface receptor on metastatic cancer cells can be exploited in the development of composite target cancer chemotherapeutics. These compounds link a specific targeting agent with a high target cell affinity, such as NVX-188, with a cytotoxic agent capable of killing the cells. The two components can be covalently linked or formulated as a nanoparticle with NVX-188 coating the nanoparticle surface, to enhance tumor specific uptake. The cytotoxic agent is then encapsulated within the nanoparticle.

Another exemplary application of the method of the invention is the treatment of benign tumors and preneoplastic conditions associated with increased vasularization, verruca vulgaris, pyogenic granuloma, rosacea, keloid scars. Ocular diseases (tumors) associated with choroidal or iris neovascularization can also be treated according to the present invention.

In addition, the method of the invention can be used to treat inflammatory diseases. Examples of such diseases include, but are not limited to, inflammatory bowel disease such as Crohn's disease and ulcerative colitis; idiopathic inflammatory myopathies such as polymyositis (PM), dermatomyositis (DM), and related conditions with increased vascularisation; and other eye inflammatory diseases.

Diseases or conditions associated with increased inflammation, such as gingivitis and mucositis (e.g. radiation- and chemotherapy-induced mucositis), may also be treated using the method of the invention. In these applications, a compound of the invention, e.g., NVX-188 and analogues, may be applied topically, for example, as a mouthwash solution for oral mucositis. To treat acne, a compound of the invention such as NVX-188 and analogues may be applied locally either alone or in combination with antibacterial or other antiphlogistic treatments. Gastrointestinal diseases especially associated with chronic inflammatory conditions such as gastritis or duodenitis may be treated using the method of the invention most efficiently by applying oral formulations of a compound of the invention (e.g., NVX-188 and analogues).

A central feature of rheumatoid arthritis is chronic inflammation leading to destruction of cartilage and bone in affected joints. This inflammation has been attributed to cytokine system activation. This is regulated by inflammatory cells and in particular through tumor necrosis factor production, IL-1 and IL-6, by activated macrophages. These macrophages express $\alpha_v\beta_3$ integrin on their surface. $\alpha_v\beta_3$ inhibitors are thus useful for rheumatoid arthritis therapies.

Immune and autoimmune diseases to be treated using the method of the invention include, but are not limited to, rheumatoid arthritis, psoriatic arthritis, psoriasis, multiple sclerosis, asthma bronchiale and allergy, and other inflammatory conditions of the skin and subcutaneous tissue.

Rheumatoid arthritis (RA) is a debilitating, systemic, autoimmune disease associated with extensive bone and cartilage destruction within the joints. There are substantial data to support the view that $\alpha_v\beta_3$ integrin plays a critical role in the pathogenesis of RA. These roles include activating macrophage-dependent inflammation, osteoclast development, bone resorption, and inflammatory angiogenesis. RA is an inflammatory disease with active angiogenesis and $\alpha_v\beta_3$ integrin vasculature expression.

Animal studies of $\alpha_v\beta_3$ inhibitors in rabbits and rats with induced arthritis, experimental models that mimic rheumatoid arthritis in man, showed reduced arthrogenic changes. These changes included synovial angiogenesis inhibition, reduced cell infiltrate, pannus formation and cartilage erosion in the rabbits, and significant protection of the bone, cartilage and soft tissue in the rats.

Psoriasis, although primarily thought to be an immunological-mediated disease, is also characterized by excessive angiogensis. A compound of the invention such as NVX-188 and analogoues may therefore be used not only systemically but preferably also topically alone or in combination with other medicaments currently used in the treatment of psoriasis. These medicaments could be, for example, added as topical lotions, ointments, creams, gels, and shampoos for the skin and scalp. FDA-approved prescription topicals to treat psoriasis include corticosteroids, retinoids, calcipotriene, and coal tar products.

Multiple sclerosis (MS) is another debilitating disease mediated by autoimmune processes. MS lesions in the central nervous system show alterations in laminin receptor expression, including $\alpha_v\beta_3$ integrin. A compound of the invention such as NVX-188 is potentially useful as a specific ligand to bind to the $\alpha_v\beta_3$ integrin receptor.

Other inflammatory conditions of the skin and subcutaneous tissue that can be treated using the method of the invention include, but are not limited to, erythematosquamous dermatosis, atopic dermatitis and related conditions, contact dermatitis and other eczema, dermatitis due to substances taken internally, bullous dermatoses, erythematous conditions, lichen, and pruritus and related conditions.

A compound of the invention, e.g., NVX-188 and analogous, may be used either systemically but most likely topically alone or in combination with other medicaments currently used. These medicaments could be, for example, added as topical lotions, ointments, creams, gels, and shampoos for the skin and scalp. Examples of conditions that may be treated are: erythematosquamous dermatosis, parakeratosis variegate, seborrheic dermatitis, seborrhea capitis, other seborrheic dermatitis, erythematosquamous dermatosis, atopic dermatitis and related conditions, erythema, atopic dermatitis, Besnier's prurigo, eczema: (atopic, flexural, intrinsic (allergic)), neurodermatitis, contact dermatitis and other eczema including dermatitis (contact, occupational), dermatitis due to substances taken internally, due to drugs and medicines in contact with skin, dermatitis (allergic), for example, due to any drug applied to skin or due to other chemical products, dermatitis due to solar radiation, sunburn, berloque dermatitis, photoallergic response dermatitis, phototoxic response dermatitis, polymorphous light eruption, disseminated superficial actinic porokeratosis (DSAP), dermatitis to due to cosmetics, dermatitis due to other radiation such as infrared rays, ultraviolet rays and due to treatment with ionizing radiation, bullous dermatoses, dermatitis herpetiformis, dermatosis herpetiformis, Duhring's disease, dermatitis herpetiformis, subcorneal pustular dermatosis, Sneddon-Wilkinson disease, juvenile dermatitis herpetiformis, juvenile pemphigoid, impetigo herpetiformis, erythema multiforme, erythema iris, herpes iris, Lyell's syndrome, lupus erythematosus, other specified erythematous conditions, such as Ritter's disease, dermatitis exfoliativa neonatorum, erythema intertrigo, lichen, lichenification and lichen simplex chronicus, Hyde's disease, neurodermatitis (circumscripta) (local), other specified pruritic conditions, and pruritus.

Furthermore, the method of the invention is useful for treating vascular diseases. The relevant vascular diseases include, but are not limited to, endometriosis, dysfunctional uterine bleeding, endometrial hyperplasia, myelofibrosis, hemangioma, arteriosclerosis, acute and chronic transplant rejection and transplant vasculopathy, ocular disorders that characterized by ocular neovascularization including age-related macular degeneration (AMD), proliferative diabetic retinopathy (PDR), retinopathy of prematurity (ROP), neovascular glaucoma, retinoblastoma, retrolental fibroplasia, rubeosis, uveitis, macular degeneration, and corneal graft neovascularization.

Age-relate macular degeneration (AMD) is a common cause of visual loss in the elderly. The most severe forms involve extensive new blood vessel formation in affected areas of the retina. For this reason, anti-angiogenic compounds have been successfully administered to inhibit ingrowth of blood vessels and preserve vision. $\alpha_v\beta_3$ integrin antagonist's angiogenesis inhibiting ability suggest that this compound may be of value in treating AMD.

Among the conditions mediated by inappropriate platelet activation, recruitment, aggregation, or thrombosis that can be treated according to the method of the invention are coronary artery disease or injury, myocardial infarction or injury following myocardial infarction, stroke, unstable angina, preeclampsia, embolism, platelet-associated ischemic disorders including lung ischemia, coronary ischemia, and cerebral ischemia, restenosis following percutaneous coronary intervention including angioplasty, atherectomy, stent placement, and bypass surgery, thrombotic disorders including coronary artery thrombosis, cerebral artery thrombosis, intracardiac thrombosis, peripheral artery thrombosis, venous thrombosis, thrombosis and coagulopathies associated with exposure to a foreign or injured tissue surface, and reocclusion following thrombosis, deep venous thrombosis (DVT), pulmonary embolism (PE), transient ischemic attacks (TIAs), and other conditions where vascular occlusion is a common underlying feature. In some embodiments, the methods according to the invention are used in individuals at high risk for thrombus formation or reformation, advanced coronary artery disease, or for occlusion, reocclusion, stenosis or restenosis of blood vessels, or stroke. In other embodiments, the methods according to the invention are used in combination with angioplasty procedures, such as balloon angioplasty, laser angioplasty, coronary atherectomy or similar techniques, carotid endarterectomy, anastomosis of vascular grafts, surgery having a high risk of thrombus formation (i.e., coronary bypass surgery, insertion of a prosthetic valve or vessel and the like), atherectomy, stent placement, placement of a chronic cardiovascular device such as an in-dwelling catheter or prosthetic valve or vessel, organ transplantation, or bypass surgery.

Other diseases and conditions that can be treated using the method of the invention include myocardial angiogenesis, hemophilic joints, vascular adhesions, sepsis, adult respirator distress syndrome, telangiectasia, and wound granulation.

Bone resorption is another area where the method of the invention can be applied. Bone resorption, such as seen in osteoporosis, involves adhesion of osteoclasts to the bone matrix. This key adhesive event is mediated by integrins. A high level of expression of $\alpha_v\beta_3$ integrin has been noted on bone-resorbing osteoclasts. Disruption of osteoclast adhesion by $\alpha_v\beta_3$ antagonists inhibits bone resorption both in vitro and in vivo.

Diseases primarily associated with pathological bone resorption include, but are not limited to, osteoporosis, Paget's disease of bone, and systemic parathormone (PTHrP)-mediated hypercalcemia.

$\alpha_v\beta_3$ antagonists have been evaluated for the prevention and treatment of osteoporosis. They have been shown to inhibit bone loss, without notable adverse effects. The need for long-term treatment in this condition dictates that any therapy will need to have a very low toxicity profile. NVX-188's high binding affinity, which may enable it to be administered at very low dose, and its apparent lack of toxicity makes this compound, as well as the other compounds of the invention, attractive for this application.

Infections with viruses which use alpha-v-beta-3 integrins as receptors for interaction with target cells in the infected organism may also be treated by a method of the invention. Exemplary viral infections include, but are not limited to, infections by Adenovirus (Adenoviridae), Coxackievirus (Picornaviridae), Echovirus (Picornaviridae), foot and mouth disease virus (Picornaviridae), Hantavirus (Buriyaviridae), human parechovirus (Picornaviridae), human immunodeficiency virus 1 (Retroviridae), and Rotavirus (Reoviridae).

A compound of the invention may be used alone, or in combination with other agents such as the therapeutic agents and imaging agents described above. The integrin and the cell may be contacted simultaneously or sequentially with the compound and the agents as mixed or individual dosages. The compound may be admixed with, or operably linked to, at least one of the agents as described above. A compound, therapeutic agent, imaging agent, or a combination thereof, may be administered parenterally, intradermally, subcutaneously, orally, transdermally, transmucosally, or rectally.

Methods of Diagnosis

A method of the invention is useful for imaging target areas, e.g., integrin receptor imaging of cancer. Therapeutic radiopharmaceuticals are pharmaceuticals comprised of a therapeutically useful radionuclide, a radioactive metal ion that emits ionizing radiation such as beta particles, alpha particles, and Auger or Coster-Kronig electrons. A compound of the invention operably linked to a radionuclide can facilitate the targeting of the radionuclide to a cell expressing an integrin. Imaging can then be performed using standard techniques of the affected areas, e.g., heart or limbs, thereby detecting the presence of a disease, or monitoring the progression of the disease or results of therapeutic treatments.

Screening Methods

One object of the invention is to provide a method of identifying integrin-binding compounds. Accordingly, the invention provides a computer-readable medium comprising a representation of a pharmacophore, wherein the pharmacophore includes features of one H-bond donor (HBD), one H-bond acceptor (HBA), two hydrophobic aromatic groups (HAR1 and HAR2), and one negatively ionizable group (NI).

In one embodiment, the HBD, HBA, HAR1, HAR2, and NI are configured according to FIG. 8A, wherein the distance between the HBD and the HRA1 is 2.81±1 Å, the distance between the HBD and the HBA is 7.52±1 Å, the distance between the HBD and the NI is 17.67±1 Å, the distance between the HRA1 and the HBA is 7.52±1 Å, the distance between the HRA1 and the HRA2 is 9.41±1 Å, the distance between the HBA and the NI is 10.20±1 Å, and the distance between the HRA2 and the NI is 5.88±1 Å. In particular, the distance between the HBD and the HRA1 may be 2.81 Å, the distance between the HBD and the HBA may be 7.52 Å, the distance between the HBD and the NI may be 17.67 Å, the distance between the HRA1 and the HBA may be 7.52 Å, the distance between the HRA1 and the HRA2 may be 9.41 Å, the distance between the HBA and the NI may be 10.20 Å, and the distance between the HRA2 and the NI may be 5.88 Å.

In another embodiment, the HBD, HBA, HAR1, HAR2, and NI are configured according to FIG. 8B, wherein the distance between the HBD and the HRA1 is 2.80±1 Å, the distance between the HBD and the HBA is 7.34±1 Å, the distance between the HBD and the NI is 16.92±1 Å, the distance between the HRA1 and the HBA is 5.20±1 Å, the distance between the HRA1 and the NI is 14.34±1 Å, the distance between the HBA and the HRA2 is 4.69±1 Å, the distance between the HBA and the NI is 9.85±1 Å, and the distance between the HRA2 and the NI is 5.66±1 Å. In particular, the distance between the HBD and the HRA1 may be 2.80 Å, the distance between the HBD and the HBA may be 7.34 Å, the distance between the HBD and the NI may be 16.92 Å, the distance between the HRA1 and the HBA may be 5.20 Å, the distance between the HRA1 and the NI may be 14.34 Å, the distance between the HBA and the HRA2 may be 4.69 Å, the distance between the HBA and the NI may be 9.85 Å, and the distance between the HRA2 and the NI may be 5.66 Å.

In still another embodiment, the HBD, HBA, HAR1, HAR2, and NI are configured according to FIG. 8C, wherein the distance between the HBD and the HRA1 is 2.79±1 Å, the distance between the HBD and the HRA2 is 11.94±1 Å, the distance between the HBD and the NI is 16.28±1 Å, the distance between the HRA1 and the HBA is 5.20±1 Å, the distance between the HRA1 and the NI is 14.64±1 Å, the distance between the HBA and the HRA2 is 4.72±1 Å, and the distance between the HRA2 and the NI is 5.63±1 Å. In particular, the distance between the HBD and the HRA1 may be 2.79 Å, the distance between the HBD and the HRA2 may be 11.94 Å, the distance between the HBD and the NI may be 16.28 Å, the distance between the HRA1 and the HBA may be 5.20 Å, the distance between the HRA1 and the NI may be 14.64 Å, the distance between the HBA and the HRA2 may be 4.72 Å, and the distance between the HRA2 and the NI may be 5.63 Å.

As used herein, "computer readable media" refers to any medium that can be read and accessed directly by a computer. Such media include, but are not limited to, magnetic storage media, such as floppy discs, hard disc storage media, and magnetic tape; optical storage media such as CD-ROM; electrical storage media such as RAM and ROM; and hybrids of these categories such as magnetic/optical storage media. A skilled artisan can readily create a computer readable medium having recorded thereon a representation of a pharmacophore of the invention using any of the methods well known in the art.

By providing a representation of a pharmacophore of the invention in computer readable form, a skilled artisan can routinely access the pharmacophore information for a variety of purposes. For example, one skilled in the art can use a pharmacophore of the invention in computer readable form to compare with compound information stored within data storage means. Search means are used to identify compounds that match the features of the pharmacophore and therefore are candidate integrin-binding molecules.

Accordingly, the invention provides a method of identifying an integrin-binding small molecule. The method comprises comparing the three-dimensional structure of a compound with the three-dimensional structure of a pharmacophore of the invention, and selecting the compound if the compound conforms to the features of the pharmacophore.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

Example I

Discovery of Small Molecule Integrin $\alpha_v\beta_3$ Antagonists as Novel Anticancer Agents Experimental Section Generation and Validation of Pharmacophore Hypotheses. The structures of the training set compounds (A-C) were built and thoroughly minimized using Catalyst (Accelrys, Inc.).[40] A set of unique conformations that can explore the accessible conformational flexibility of each compound were generated using Catconf module of Catalyst. The poling algorithm implemented within the Catalyst was used to generate conformations. The poling algorithm promotes high conformational variation and assures broad coverage of low energy conformational space.[49-51] The common feature pharmacophore hypotheses were generated using the HipHop algorithm of Catalyst. HipHop generates 10 pharmacophore models with its default settings. HipHop takes a collection of conformational models of the training set molecules and a selection of chemical features and identifies configurations of features common to the training set molecules. Compound A was considered as a principle compound in the pharmacophore hypotheses generation experiment. On the basis of structural and chemical features of the training set compounds and the $\alpha_v\beta_3$ active site features, a set of pharmacophoric features were selected in the beginning of the pharmacophore generation experiment. A searchable multi-conformer database of the known $\alpha_v\beta_3$ antagonists was generated using Catalyst database server. This database was used to validate the pharmacophore models.

Docking Studies. Docking was performed using version 1.2 of the GOLD program (Genetic Optimization for Ligand Docking).[42] GOLD is an automated docking program that uses genetic algorithm to explore the ligand conformational flexibility with partial flexibility of the active site.[52] The algorithm was tested on a dataset of over 300 complexes extracted from the Brookhaven Protein DataBank. GOLD succeeded in more than 70% cases in reproducing the experimental bound conformation of the ligand.[53] GOLD requires a user defined binding site. It searches for a cavity within the defined area and considers all the solvent accessible atoms in the defined area as active site atoms. Appropriate protonation states were assigned for the acidic and basic amino acid residues. All the water molecules present in the receptor were removed and hydrogen atoms were added to the integrin $\alpha_v\beta_3$ receptor. All conformers of each molecule were docked onto the $\alpha_v\beta_3$ receptor active site. At the end of each run GOLD separates and ranks all the generated bound conformations based on the fitness score and root mean square distances (RMSD). All docking runs were carried out using standard default settings with a population size of 100, a maximum number of 100,000 operations, and a mutation and crossover rate of 95. The fitness function that is implemented in GOLD consists of H-bonding, complex energy, and the ligand internal energy terms. The docking studies were performed on a 24-CPU Silicon Graphics Onyx workstation.

Cell Culture. Human breast cancer cells (MCF-7, $\alpha_v\beta_3$—, overexpressed wild-type p53, ER+; MDA-MB 468, p53 mutant, ER+; and MDA-MB-435, $\alpha_v\beta_3$+, p53 mutant, ER−) and non-small cell lung cancer cells H1975 were obtained from the American Type Cell Culture (Rockville, Md. Q4). The HEY human ovarian carcinoma cell line naturally resistant to cisplatin (CDDP) was kindly provided by Dr. Dubeau (University of Southern California Norris Cancer Center). Cells were maintained as monolayer cultures in RPMI 1640 supplemented with 10% fetal bovine serum (Gemini-Bioproducts, Woodland, Calif.) and 2 mmol/L L-glutamine at 37° C. in a humidified atmosphere of 5% $CO_2$. To remove the adherent cells from the flask for passaging and counting, cells were washed with PBS without calcium or magnesium, incubated with a small volume of 0.25% trypsin-EDTA solution (Sigma, St. Louis, Mo.) for 5 to 10 minutes, and washed with culture medium and centrifuged. All experiments were done using cells in exponential cell growth.

Drugs. A 10 mM stock solution of all compounds were prepared in DMSO and stored at −20° C. Further dilutions were freshly made in PBS.

Receptor Binding Assay. Binding affinity of all compounds on the surface of NCI-H1975 cells was determined in competitive binding experiments using $^{125}$I-labeled echistatin as radioligand as described in the literature with modifications.[41] In brief, NCI-H1975 cells were harvested, washed twice with PBS, and resuspended ($2\times10^6$ cells/mL) in binding buffer (20 mM Tris, pH 7.4, 150 mM NaCl, 2 mM $CaCl_2$, 1 mM $MgCl_2$, 1 mM $MnCl_2$, 0.1% BSA). 96-Well multiscreen DV plate (filter pore size: 0.65 μm, Millipore, Billerica, Mass.) was incubated with $^{125}$I-echistatin (50,000 cpm/well) in the presence of increasing concentrations of $\alpha_v\beta_3$ antagonists. The total incubation volume was adjusted to 200 μL. After the cells were incubated for 3 h at room temperature, the plate was filtered through multiscreen vacuum manifold and washed twice with cold binding buffer. The hydrophilic PVDF filters were collected, and the radioactivity was determined using NaI(Tl) gamma counter (Packard, Meriden, Conn.). The best-fit $IC_{50}$ values were calculated by fitting the data by nonlinear regression using GraphPad Prism (GraphPad Software, Inc., San Diego, Calif.). Experiments were carried out with triplicate samples.

Cytotoxicity Assay. Cytotoxicity was assessed by 3-(4,5-dimethylthiazol-2-yl)-2,5-diphenyltetrazolium bromide (MTT) assay as previously described.[41,54] Briefly, cells were seeded in 96-well microtiter plates and allowed to attach. Cells were subsequently treated with a continuous exposure to the corresponding drug for 72 hours. An MTT solution (at a final concentration of 0.5 mg/mL) was added to each well and cells were incubated for 4 hours at 37° C. After removal of the medium, DMSO was added and the absorbance was read at 570 nm. All assays were done in triplicate. The $IC_{50}$ was then determined for each drug from a plot of log (drug concentration) versus percentage of cell kill.

Results and Discussion

Figure 1:
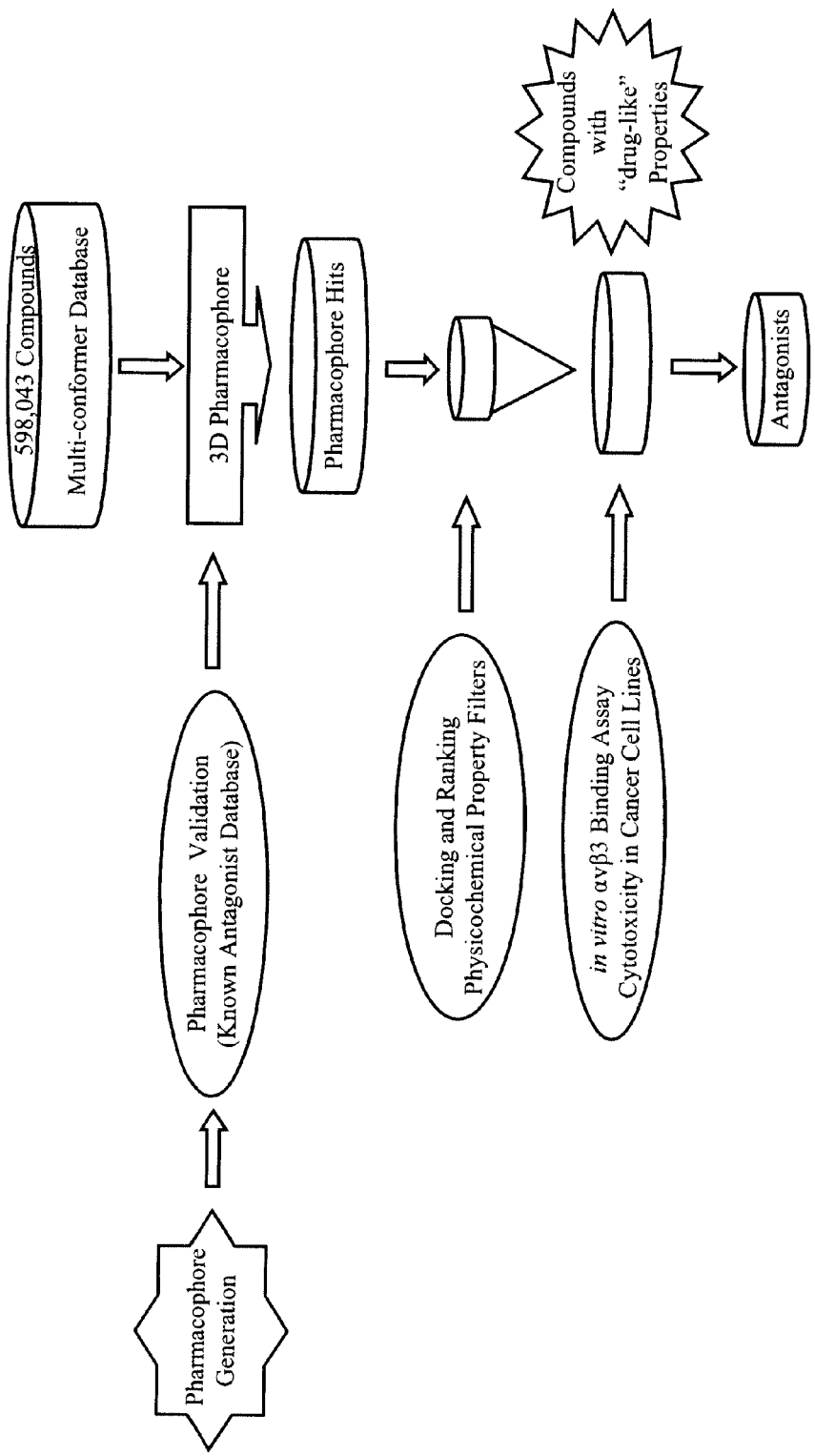
FIG. 1 is a schematic representation of pharmacophore guided design and discovery of novel $\alpha_v\beta_3$ antagonists.

Design of Integrin $\alpha_v\beta_3$ Antagonists. Previous studies using cyclic RGD peptides suggested that $\alpha_v\beta_3$ recognizes a short overall separation between the key guanidine (Arg) and carboxylic acid (Asp) groups (distance between Cβ atoms of Arg and Asp residues) of the RGD tripeptide sequence.[35, 36] Cyclic RGD peptides with a kink in the backbone conformation demonstrated more selectivity towards $\alpha_v\beta_3$ than other integrins.[24] This cyclic RGD peptide-$\alpha_v\beta_3$ interaction model provided the starting point for discovery of a variety of small-molecule peptidomimetic antagonists. The crystal structure of the extracellular segment of $\alpha_v\beta_3$ and its complex with a cyclic RGD peptide has been previously reported.[37, 38] We utilized a set of recently reported small-molecule $\alpha_v\beta_3$ antagonists to generate common feature pharmacophore models, which were then validated against a database of 638 known $\alpha_v\beta_3$ antagonists.[39] The validated pharmacophore models were used as search queries to retrieve molecules with novel structural scaffolds and desired chemical features. Our strategy to identify and design novel $\alpha_v\beta_3$ antagonists is schematically shown in FIG. 1.

Figure 2:
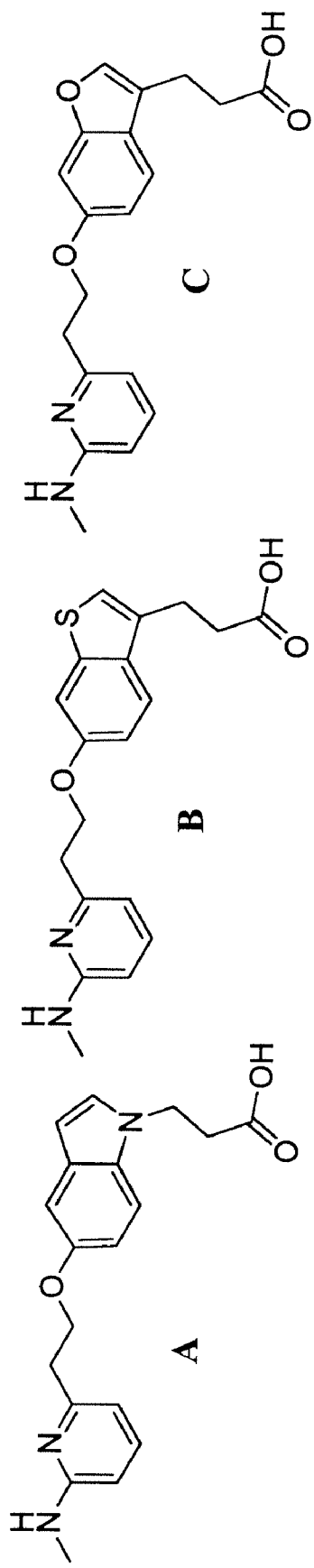
FIG. 2 shows the structures of the training set compounds A-C.

Generation of Common Feature Pharmacophore Models. Generally, the training set for generation of common feature pharmacophore models should include compounds with similar activity profiles and active site binding mechanisms, to increase the likelihood that these training compounds have comparable 3D arrangements of features that are responsible for their biological activity. The HipHop algorithm in the Catalyst software package was applied to a training set consisting of three recently reported antagonists of $\alpha_v\beta_3$ integrin (A, B and C), with comparable binding affinities to $\alpha_v\beta_3$ integrin in the range of 30 to 49 nM (FIG. 2), to derive common feature pharmacophore models.[39, 40] The training set compounds were close analogues and expected to bind to a similar site on the active site of $\alpha_v\beta_3$ receptor in a similar binding conformation. The pharmacophoric features were selected on the basis of (1) the structural and chemical features of the training set antagonists, (2) the architecture of $\alpha_v\beta_3$ receptor active site, and (3) the critical interactions observed between the cyclic-RGD peptide and prominent $\alpha_v\beta_3$ receptor active residues in the co-crystal structure of the $\alpha_v\beta_3$ receptor complexed with the cyclic-RGD peptide (PDB1L5G).[37] The features considered in the pharmacophore model generation experiment were H-bond donor (HBD), H-bond acceptor (HBA), ring aromatic (HYR), hydrophobic (HYA), and negatively ionizable (NI) feature. HipHop generated 10 five-featured pharmacophore hypotheses. While these hypotheses were similar in their pharmacophoric features, the relative orientation, position, and vector directions of various features were different. Cluster analysis of the 10 hypotheses using a hierarchical complete linkage method available in the Catalyst program produced three clusters. A representative model from each of the three clusters (pharmacophore hypotheses Hypo1, Hypo5 and Hypo9) were selected for further analyses and validation.

Figure 3:
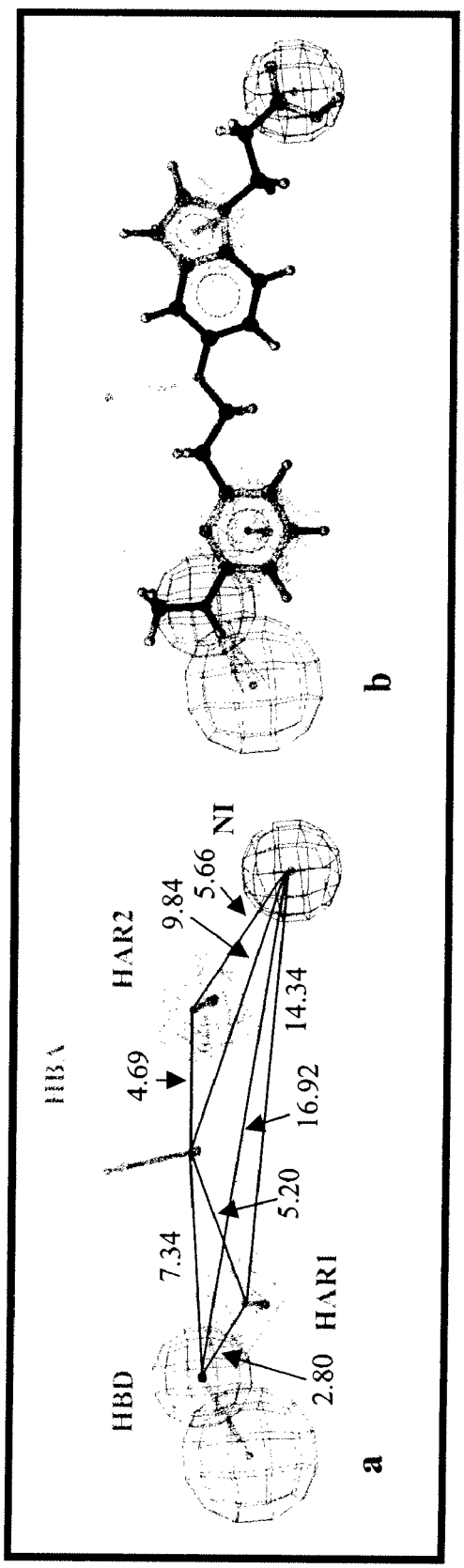
FIG. 3. (a) The common feature pharmacophore Hypo5. (b) Hypo5 is mapped onto one of the training set compounds, A. The important chemical features of compound A are mapped by pharmacophoric features of Hypo5. The pharmacophore features are shown as H-bond donor (HBD) in magenta, H-bond acceptor (HBA) in green, hydrophobic aromatic (HAR1-HAR2) in brown, and negatively ionizable feature (NI) in blue. The inter-feature distances are given in Å.
Figure 4:
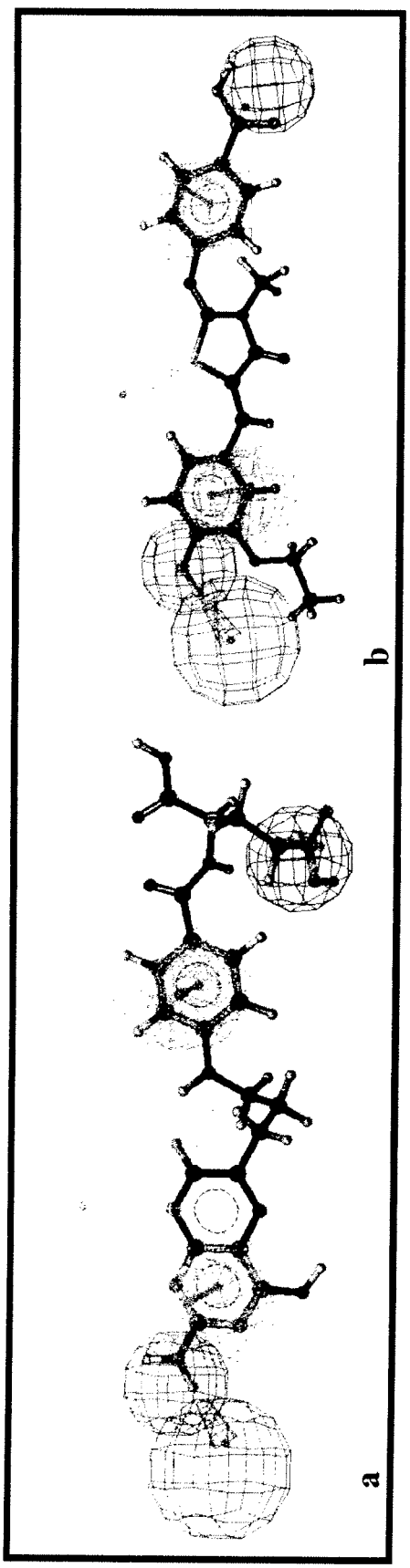
FIG. 4 illustrates mapping of Hypo5 onto novel $\alpha_v\beta_3$ receptor antagonists AV3 (a), and AV26 (b). The pharmacophoric features of Hypo5 are reasonably mapped onto key chemical features of the antagonists. The pharmacophore features are shown as H-bond donor in magenta, H-bond acceptor in green, hydrophobic aromatic in brown, and negatively ionizable feature in blue.
Figure 5:
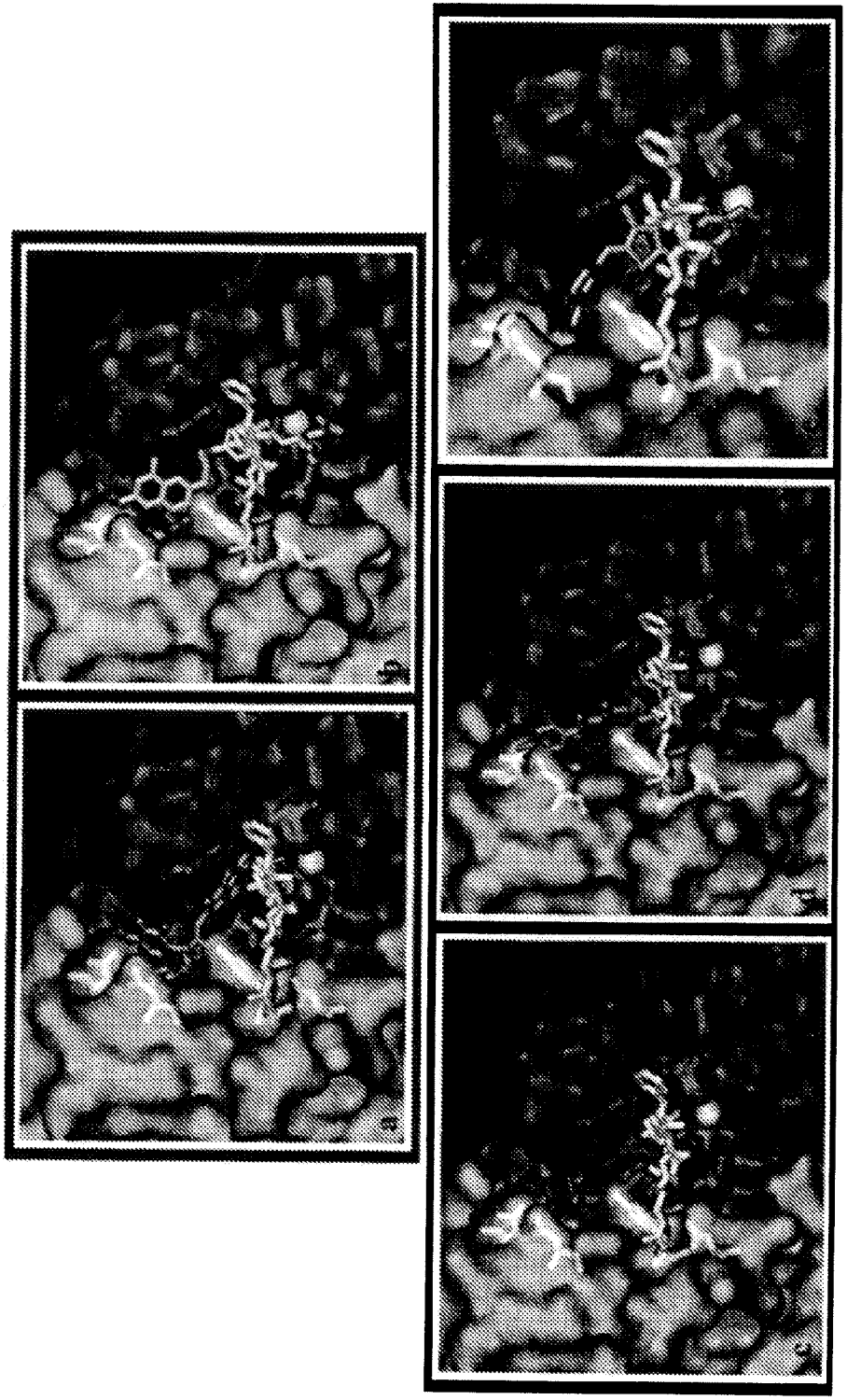
FIG. 5 depicts predicted bound conformation of antagonists A (a), AV3 (b), AV26 (c), AV27 (d), and AV38 (e) inside the $\alpha_v\beta_3$ RGD peptide binding site. The yellow and red parts represent $\alpha$ and $\beta$ chains of $\alpha_v\beta_3$ receptor. The prominent active site amino acid residues are shown as stick models on the receptor surface. The green stick model represents the bound orientation of the cyclic-RGD peptide (PDB1L5G). The active site $Mn^{2+}$ (MIDAS) is shown as a cyan sphere.

Validation of Common Features Pharmacophores. As an internal validation, the training set compounds A-C were mapped onto the three pharmacophores. The fit scores and associated energy of mapped conformations of the training set compounds (Table 1) yielded a lower energy for Hypo5 than Hypo1 or Hypo9 for compounds A and B, but a relatively high energy for compound C. The mapping of Hypo5 onto compound A, shown in FIG. 3, confirms a good agreement between critical chemical features of this compound and the pharmacophore.

TABLE 1

Mapping of the Training Set Compounds (A-C) by Hypo1, Hypo5, and Hypo9

| | training set compounds | | | | | |
|---|---|---|---|---|---|---|
| | A | | B | | C | |
| Hypothesis | fit score | conformation energy (Kcal/mol) | fit score | conformation energy (Kcal/mol) | fit score | conformation energy (Kcal/mol) |
| Hypo1 | 4.99 | 19.41 | 4.98 | 14.25 | 4.90 | 4.42 |
| Hypo5 | 4.99 | 6.15 | 4.94 | 5.02 | 4.8 | 13.54 |
| Hypo9 | 5.00 | 16.28 | 4.87 | 18.19 | 4.61 | 7.83 |

In order to evaluate the discriminative ability of these pharmacophores in the separation of potent antagonists from inactive compounds, the three representative pharmacophores were used as 3D queries to search a database of known $\alpha_v\beta_3$ receptor antagonists. This database has a total of 638 compounds with a wide range of activity profiles against $\alpha_v\beta_3$ receptor. Of the 638 compounds, 303, which showed $\alpha_v\beta_3$ receptor inhibition at $IC_{50}$ values ≦20 nM were considered potent $\alpha_v\beta_3$ antagonists. Search results are summarized in Table 2. Hypo5 performed better than the other two pharmacophores retrieving 147 compounds, of which 88 (~60%) compounds were potent antagonists of $\alpha_v\beta_3$. Hypo9 retrieved more active compounds, but the percent of these considered potent was lower (~54%) than for Hypo5. On the basis of Hypo5's superior ability to select potent antagonists, and the match of Hypo5 to two of the three training set compounds, this pharmacophore was selected for the next step: a 3D query to search a subset of our in-house databases to retrieve compounds with novel structural scaffolds and desired features.

TABLE 2

Validation of Common Feature Pharmacophore Models Hypo1, Hypo5, and Hypo9 against a Database of Known Integrin $\alpha_v\beta_3$ Antagonists (n = 638)

| hypothesis | total hits | active hits | inactive hits | % active |
|---|---|---|---|---|
| Hypo1 | 89 | 51 | 38 | 57.3 |
| Hypo5 | 147 | 88 | 59 | 59.9 |
| Hypo9 | 182 | 98 | 84 | 53.8 |

Database Search and Compound Selection. A search of the NCI2000 database of 238,819 compounds using Hypo5 yielded 684 hits. Of the 684 compounds retrieved by Hypo5, 282 compounds with molecular weight ≦500 were considered for further physicochemical property analysis and the remaining were discarded. A search of the Chemical Diversity (ChemDiv, Inc, San Diego, Calif.) database of 359,224 compounds produced 148 hits. A physicochemical property filter was used to eliminate compounds that did not possess drug-like properties prior to in vitro screening.[41] On the basis of pharmacophore fit value, calculated physicochemical properties, structural diversity, and sample availability, 8 compounds were obtained from the NCI compound repository and a collection of 21 compounds were purchased from Chemical Diversity for in vitro evaluation.

$\alpha_v\beta_3$ Binding. Receptor binding affinity of all compounds on the surface of non-small cell lung cancer NCI-H1975 cells was determined in competitive binding experiments using $^{125}$I-labeled echistatin as radioligand and the results are presented in Table 3. Of the 29 compounds tested, four compounds showed remarkable $\alpha_v\beta_3$ binding affinity (AV3=52 nM, AV26=240 nM, AV27=18 nM, AV32=605 nM). Two compounds, AV3 and AV27 showed a similar range of binding affinity as the training set compounds A-C (30-49 nM).[39] As observed in the validation analysis, Hypo5 was successful in the retrieval of structurally diverse potent antagonists of $\alpha_v\beta_3$ with nanomolar binding affinity. These compounds represent a novel set of antagonists with diverse structural scaffolds. Unlike the training set compounds, the compounds possessed several functional groups of hydrophilic nature. This is an important feature considering the highly electrostatic nature of the RGD peptide binding region of $\alpha_v\beta_3$. The RGD peptide forms strong electrostatic interactions through its two charged ends with $\alpha_v\beta_3$ in the $\alpha_v\beta_3$-cyclic RGD peptide complex crystal structure. Compounds AV3, AV27, and AV32 broadly fall into a RGD mimetic antagonist category, since they have a carboxylate group or amine/amide group, at either ends that can establish similar electrostatic interactions with $\alpha_v\beta_3$. Additionally, presence of several hydrophilic functional groups on these compounds favors their interaction with the highly electrostatic region of the RGD binding site of $\alpha_v\beta_3$. Given these interesting structural features, we tested additional structurally close analogues of AV27 and AV32. However, substructure search queries using the core scaffolds of these compounds in our in-house databases yield no close analogues. Structure-activity studies around the core scaffolds of these two compounds might be an alternative option to further optimize their binding affinity towards $\alpha_v\beta_3$. Possessing unique structural features, AV26 represents a novel non-RGD mimetic class of $\alpha_v\beta_3$ antagonists. We carried out a limited structure-activity relationship (SAR) analysis on compound AV26 by testing compounds AV34-AV38 in our binding assay (Table 3). The substructure search using the core scaffold of AV26 as a search query retrieved few compounds from our in-house database of 359,224 compounds. The analogues AV34-AV38 were purchased from Chemical Diversity (San Diego, Calif.) and screened for their $\alpha_v\beta_3$ binding affinity. From this SAR study we discovered two new compounds: AV35 with IC$_{50}$ value of 24 nM showed 10-fold higher affinity than the parent compound AV26. AV38 with IC$_{50}$ value of 0.03 nM was the most potent and showed 800-fold higher affinity than the parent AV26. Compounds AV26, AV35, and AV38 deviate structurally from conventional RGD mimetic $\alpha_v\beta_3$ antagonists, suggesting that they represent a novel class of non-RGD mimetic antagonists of $\alpha_v\beta_3$ with novel modes of interaction. To our knowledge, these compounds are among the most potent $\alpha_v\beta_3$ antagonists described thus far. Together, our six compounds represent novel small-molecule $\alpha_v\beta_3$ antagonists, and studies are underway to demonstrate their in vivo efficacy as anticancer agents. Studies are also underway to selectively deliver cytotoxic agents such as paclitaxel to $\alpha_v\beta_3$ overexpressing cancers through covalent conjugation.

TABLE 3

Novel $\alpha_v\beta_3$ Antagonists Discovered through Pharmacophore-based Database Searching

| compd. | structure | drug-like physicochemical properties[a] | | | | | | $\alpha_v\beta_3$ binding affinity (nM) |
|---|---|---|---|---|---|---|---|---|
| | | MW | HBA | HBD | logP | Rb | PSA | |
| AV3 | 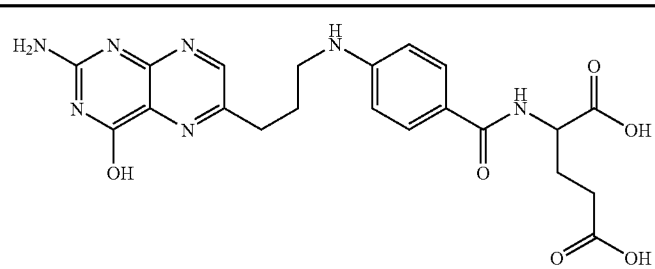 | 469 | 13 | 7 | 0.7 | 15 | 332 | 52 |
| AV26 | 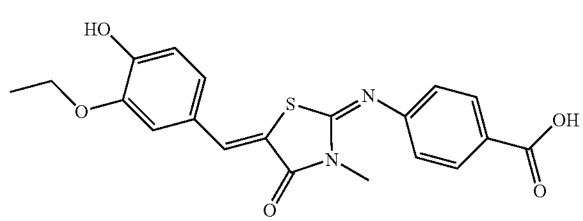 | 398 | 7 | 2 | 3.6 | 7 | 148 | 240 |
| AV27 | 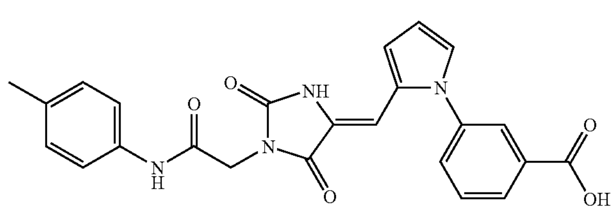 | 444 | 9 | 3 | 2.7 | 8 | 191 | 18 |

TABLE 3-continued

Novel α$_v$β$_3$ Antagonists Discovered through Pharmacophore-based Database Searching

| compd. | structure | drug-like physicochemical properties[a] | | | | | | α$_v$β$_3$ binding affinity |
|---|---|---|---|---|---|---|---|---|
| | | MW | HBA | HBD | logP | Rb | PSA | (nM) |
| AV32 | 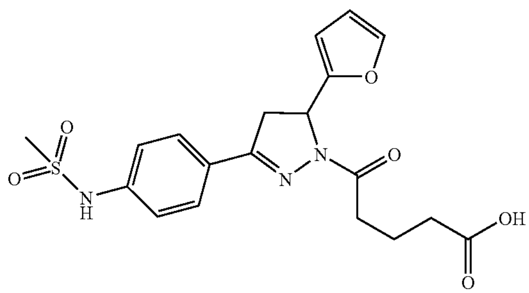 | 419 | 9 | 2 | 0.7 | 10 | 182 | 605 |
| AV35[b] | 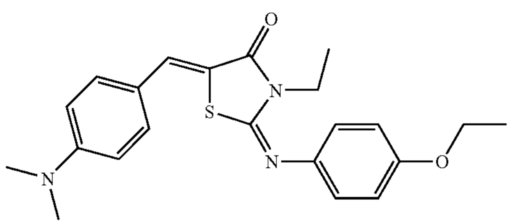 | 395 | 5 | 0 | 4.82 | 6 | 37.9 | 24 |
| AV38 | 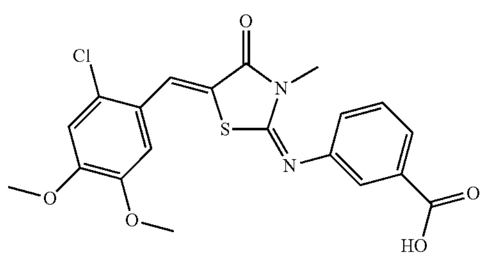 | 432 | 7 | 1 | 4.22 | 6 | 130 | 0.03 |

[a]MW: molecular weight, Drug-like properties: HBA: number of hydrogen-bond acceptor. HBD: number of hydrogen-bond donor, AlogP98: logarithm of the octanol-water partition coefficient, Rb: number of rotatable bond. PSA: 3D-polar surface area (Calculated using a Simulations Plus model).
[b]Compounds AV34-AV38 are analogues of compound AV26.

TABLE S1

Structures of Compounds AV1-2, 4-11, 14-15, 17-25, 28-31, 34, and 36-37.

| compd. | structure |
|---|---|
| AV1 | 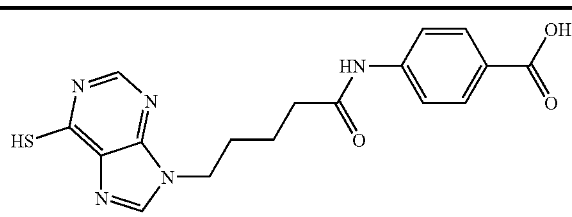 |
| AV2 | 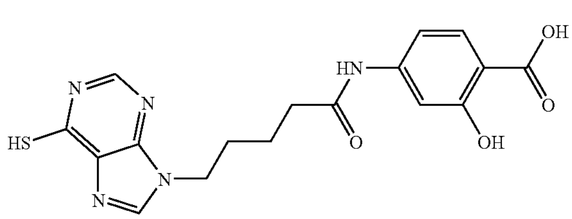 |

TABLE S1-continued

Structures of Compounds AV1-2, 4-11, 14-15, 17-25, 28-31, 34, and 36-37.

| compd. | structure |
| --- | --- |
| AV4 | 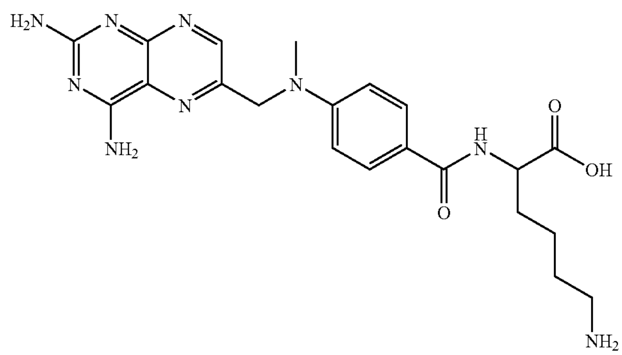 |
| AV5 | 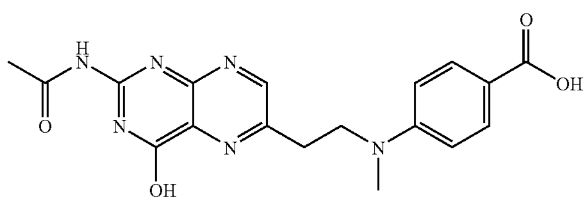 |
| AV6 | 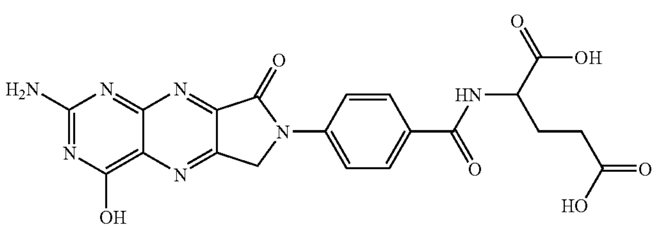 |
| AV7 | 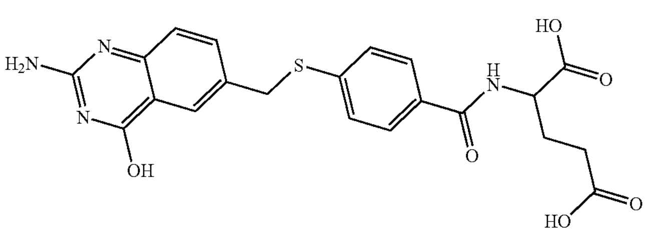 |
| AV8 | 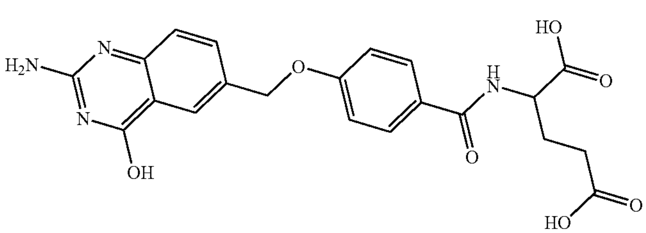 |
| AV9 | 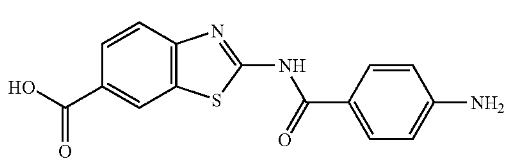 |

TABLE S1-continued

Structures of Compounds AV1-2, 4-11, 14-15, 17-25, 28-31, 34, and 36-37.

| compd. | structure |
|---|---|
| AV10 | 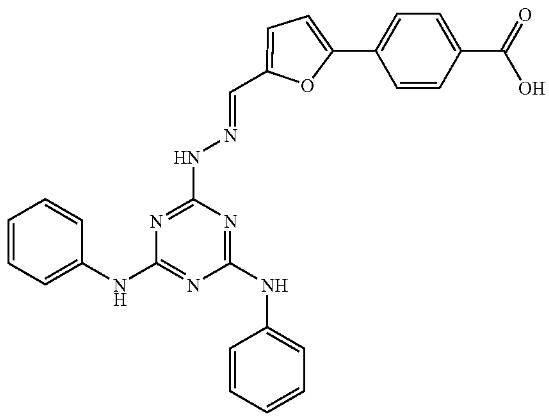 |
| AV11 | 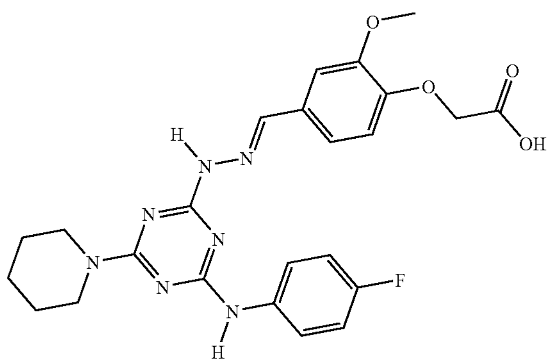 |
| AV14 | 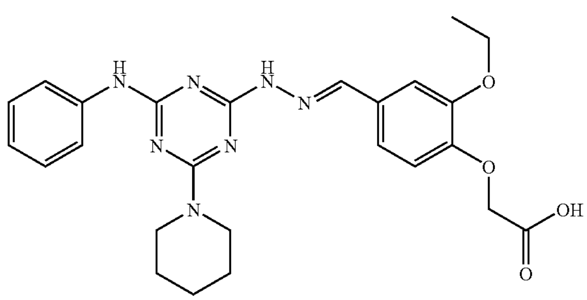 |
| AV15 | 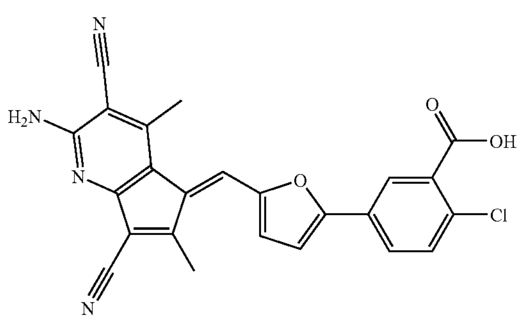 |

TABLE S1-continued

Structures of Compounds AV1-2, 4-11, 14-15, 17-25, 28-31, 34, and 36-37.

| compd. | structure |
|---|---|
| AV17 | 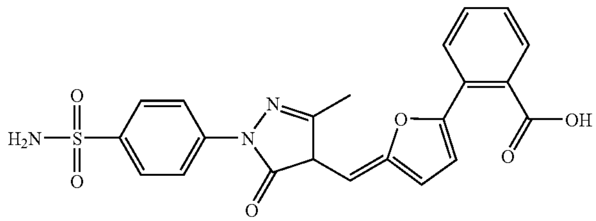 |
| AV18 | 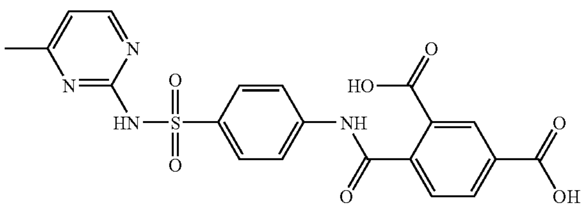 |
| AV19 | 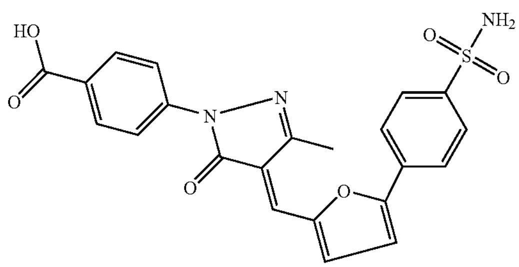 |
| AV20 | 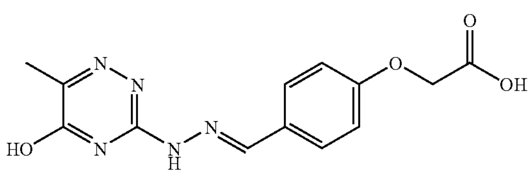 |
| AV21 | 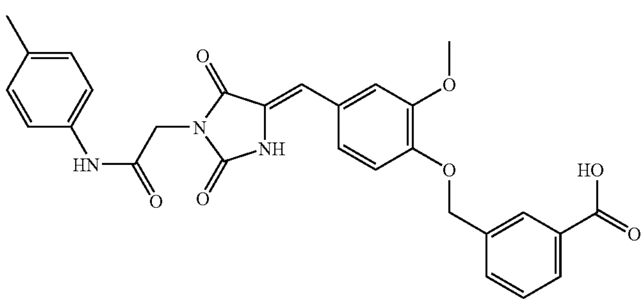 |
| AV22 | 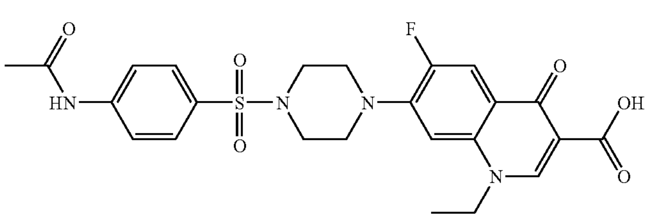 |

TABLE S1-continued

Structures of Compounds AV1-2, 4-11, 14-15, 17-25, 28-31, 34, and 36-37.

| compd. | structure |
|---|---|
| AV23 | 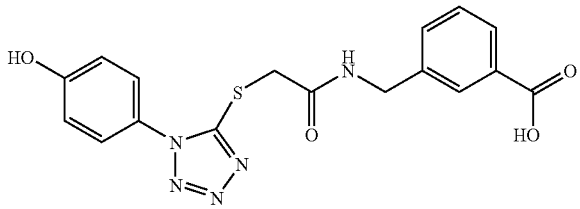 |
| AV24 | 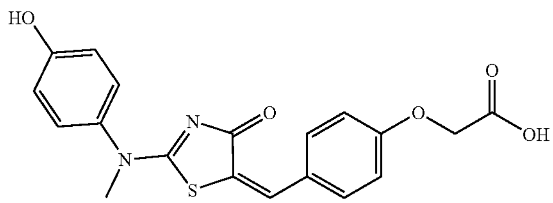 |
| AV25 | 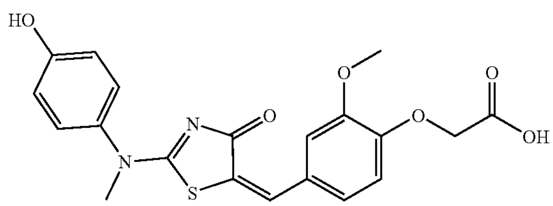 |
| AV28 | 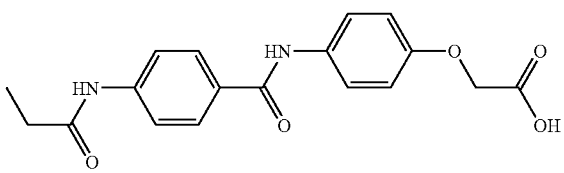 |
| AV29 | 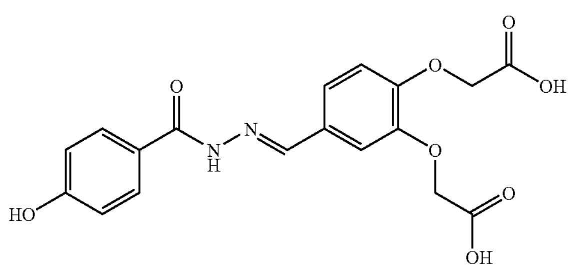 |
| AV30 | 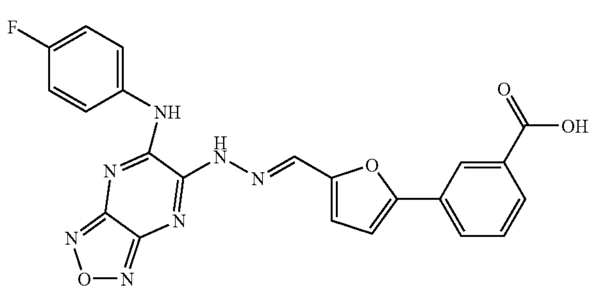 |
| AV31 | 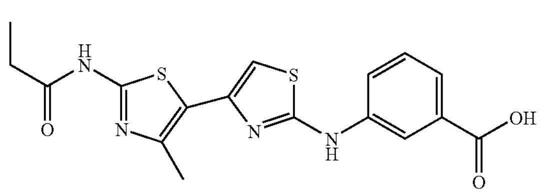 |

TABLE S1-continued

Structures of Compounds AV1-2, 4-11, 14-15, 17-25, 28-31, 34, and 36-37.

| compd. | structure |
|---|---|
| AV34 | [chemical structure] |
| AV36 | [chemical structure] |
| AV37 | [chemical structure] |

Cytotoxicity of Selected Compounds in a Panel of Cancer Cell lines. Initially, we tested all compounds in two breast cancer cell lines MDA-MB-435 and MCF7 with high and low $\alpha_v\beta_3$ expression as well as in HEY ovarian cancer cell line naturally resistant to cisplatin. Compounds that showed significant inhibition of cell growth at 20 μM (Table 4) were subsequently tested in a panel of five cell lines (Table 5). We observed a remarkable specificity for some of the compounds against these cells. For example, AV26 showed more than 60 fold selectivity for MDA-MB-435 cells as compared to the MCF7, NIH3T3, and CRL5908 cells and close to 40 fold selectivity than the HEY cells. A similar trend, but smaller magnitude, was observed with compound AV34. On the other hand, AV30 showed a profile very similar in MDA-MB-435, HEY, and NIH3T3 cells, but was significantly less active against MCF-7 and NCI-H1975 cells. Interestingly, none of the novel antagonists except AV26 showed notable cytotoxicity, which indicates that these novel antagonists may have utility as non-cytotoxic mechanism based anticancer therapeutics. Considering the fact that $\alpha_v\beta_3$ mediates migration, attachment and apoptosis of cancer cells, the combination of these novel high affinity antagonists with conventional cytotoxic drugs should show improved therapeutic benefits without additional toxicity.

TABLE 4

Cytotoxicity of Compounds AVI-AV38 in a Panel of Cancer Cell Lines

| | % inhibition of cell growth at 20 μM | | |
|---|---|---|---|
| compd. | 435[a] | MCF7[b] | HEY[c] |
| AV1 | 0 | 0 | 14 |
| AV2 | 1 | 1 | 0 |
| AV3 | 0 | 0 | 0 |
| AV4 | 16 | 30 | 0 |
| AV5 | 49 | 0 | 0 |
| AV6 | 12 | 19 | 0 |
| AV7 | 5 | 22 | 0 |
| AV8 | 12 | 24 | 6 |
| AV9 | 19 | 36 | 0 |
| AV10 | 93 | 62 | 73 |
| AV11 | 53 | 49 | 0 |
| AV14 | 70 | 3 | 0 |
| AV15 | 33 | 14 | 14 |
| AV17 | 24 | 20 | 5 |
| AV18 | 18 | 11 | 0 |
| AV19 | 30 | 66 | 6 |
| AV20 | 11 | 27 | 0 |
| AV21 | 26 | 43 | 0 |
| AV22 | 25 | 7 | 0 |
| AV23 | 9 | 34 | 0 |
| AV24 | 9 | 21 | 19 |

TABLE 4-continued

Cytotoxicity of Compounds AVI-AV38
in a Panel of Cancer Cell Lines

| | % inhibition of cell growth at 20 μM | | |
|---|---|---|---|
| compd. | 435[a] | MCF7[b] | HEY[c] |
| AV25 | 26 | 29 | 12 |
| AV26 | 94 | 37 | 51 |
| AV27 | 0 | 0 | 5 |
| AV28 | 32 | 32 | 34 |
| AV29 | 14 | 21 | 9 |
| AV30 | 71 | 52 | 90 |
| AV31 | 21 | 44 | 62 |
| AV32 | 0 | 26 | 18 |
| AV34 | 65 | 31 | 25 |
| AV35 | 26 | 36 | 17 |
| AV36 | 16 | 29 | 4 |
| AV37 | 3 | 9 | 0 |
| AV38 | 0 | 18 | 0 |

[a]435: MDA-MB-435, breast cancer cell line;
[b]MCF7: breast cancer cell lines,
[c]HEY: ovarian cancer cell line.

TABLE 5

Cytotoxicity of Selected Compounds
in a Panel of Cancer Cell Lines

| | cytotoxicity in a panel of cancer cell-lines (IC$_{50}$, (μM) | | | | |
|---|---|---|---|---|---|
| compd. | 435[a] | MCF-7[b] | NIH3T3[c] | HEY[d] | NCI-H1975[e] |
| AV3 | >20 | >20 | >20 | >20 | >20 |
| AV10 | 18 ± 9 | >20 | — | 21 ± 3 | — |
| AV19 | >20 | 19 ± 4 | — | >20 | — |
| AV26 | 0.34 ± 0.06 | >20 | >20 | 13 ± 8 | >20 |
| AV27 | >20 | >20 | >20 | >20 | >20 |
| AV30 | 8 ± 0.50 | 19 ± 4 | 13 ± 3 | 7 ± 0.42 | >20 |
| AV32 | >20 | >20 | >20 | >20 | >20 |
| AV34 | 2.8 ± 0.01 | >20 | — | >20 | — |
| AV35 | >20 | >20 | >20 | >20 | >20 |
| AV38 | >20 | >20 | >20 | >20 | >20 |

[a]435: MDA-MB-435, breast cancer cell line;
[d]HEY: ovarian cancer cell line;
[b]MCF-7: breast cancer cell line;
[e]NCI-H1975: lung cancer cell-line;
[c]NIH3T3: mouse fibroblast.

Figure 6:
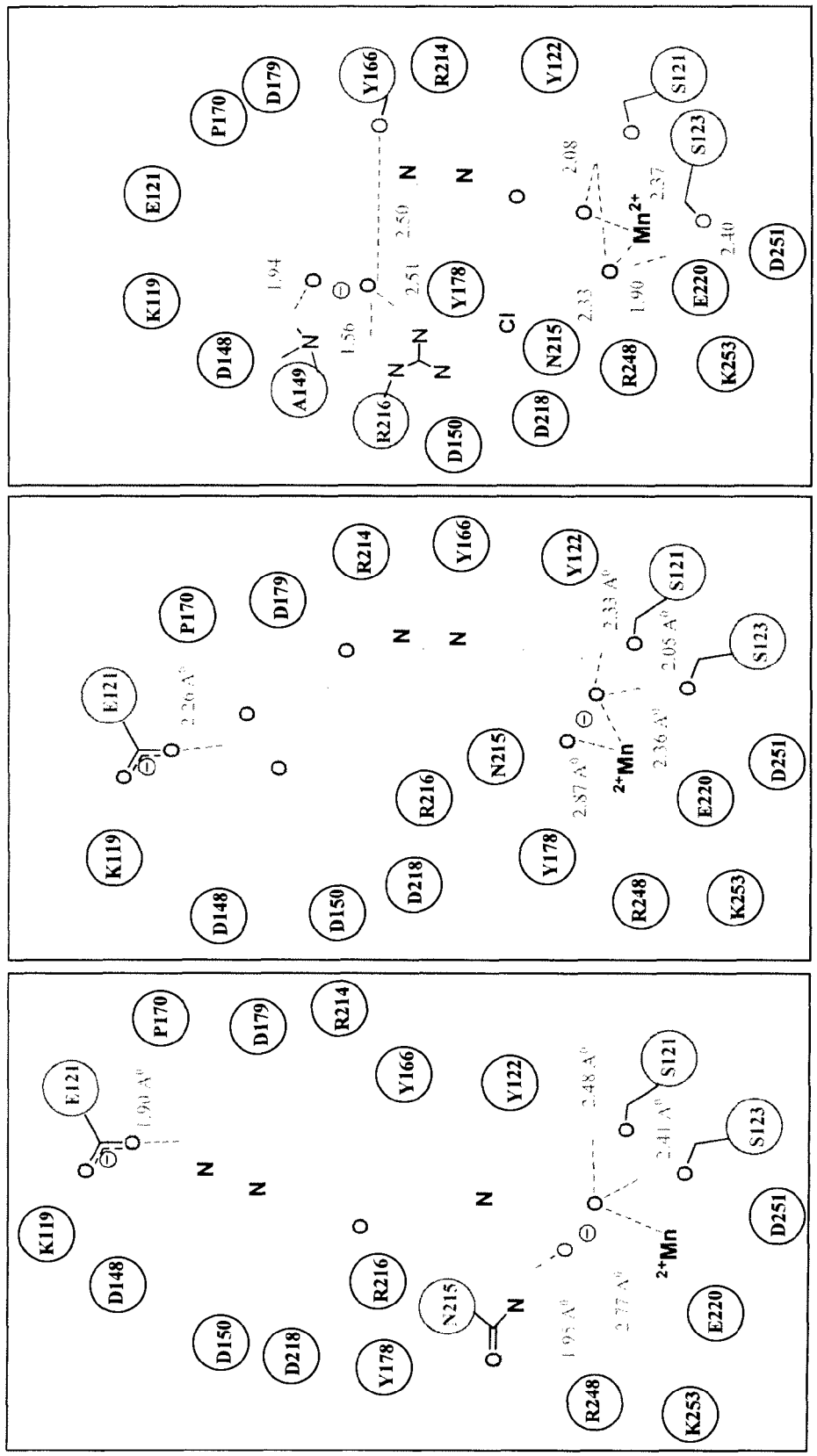
FIG. 6 is a schematic representation of observed interactions between antagonists A (a), AV26 (b), and AV38 (c) and prominent amino acid residues on $\alpha_v\beta_3$ RGD peptide binding site. The dashed lines represent H-bonding interactions. H-bonding distances are given in Å.

Docking Studies. In order to identify binding orientations of our novel antagonists, we have docked compounds A, AV3, AV26, AV27, and AV38 onto the $\alpha_v\beta_3$ RGD binding region using GOLD.[42] The predicted bound conformations of compounds A, AV3, AV26, AV27, and AV38 inside the $\alpha_v\beta_3$ RGD binding region are shown in FIG. 5a-e. GOLD generated several feasible bound conformations for each compound and ranked them according to their fitness scores. The bound conformation with the most favorable energies was considered the best binding orientation. In the crystal structure of $\alpha_v\beta_3$ receptor complexed with the cyclic RGD peptide, one of the Asp carboxylate oxygens of the cyclic RGD peptide interacts with a $Mn^{2+}$ at MIDAS (Metal Ion-Dependent Adhesion Site) in β chain of $\alpha_v\beta_3$ receptor while its Arg guanidinium group interacts with D218 of β chain and D150 of α chain of $\alpha_v\beta_3$ receptor (PDB1L5G). Compounds A, AV3, AV26, and AV27 established similar binding interactions at their carboxylate end with the $Mn^{2+}$ of MIDAS, as well as forming several H-bonding interactions with the side chain hydroxyl groups of amino acid residues S121 and S123. In contrast to the bound orientation of Arg side chain of the cyclic RGD peptide, the amine/amide bearing end of compounds A, AV3, AV27 and the hydroxyl bearing phenyl group of AV26 occupied a cavity away from D218 of β chain but close to D150 of α chain. This cavity is surrounded by amino acid residues Y166, P170, D179, R214, N215, and R216 from β chain and amino acid residues K119, E121, D148, D150, Y178, and R248 from α chain of $\alpha_v\beta_3$. Strikingly, the most potent non-RGD mimetic antagonist AV38 adopted a reverse binding orientation and established a set of strong electrostatic interactions with various amino acid residues within the cyclic RGD peptide binding region of $\alpha_v\beta_3$. The schematic presentation of observed key interactions between compounds A, AV26, and AV38 and various amino acid resides at the $\alpha_v\beta_3$ RGD peptide binding site is shown in FIG. 6. The dimethoxy bearing phenyl group of AV38 occupied an area close to $Mn^{2+}$ of MIDAS and two methoxy oxygen atoms coordinated to $Mn^{2+}$. Three H-binding interactions observed between the methoxy oxygen atoms and the hydroxyl groups of amino acid residues S121 and S123. The carboxylate bearing phenyl group occupied an area surrounded by amino acid residues Y116, P170, D179, R214, and R216 from β chain and D148, A149, D150, and Y178 from α chain of $\alpha_v\beta_3$. The carboxylate oxygen atoms formed several strong H-bonding interactions with R216 guanidinium group, the backbone NH of A149 and the hydroxyl group of Y166. A consistent pattern was observed in the predicted binding orientations of all the antagonists except the most potent antagonist AV38. The functional groups of these antagonists with similar chemical nature occupied similar areas in the $\alpha_v\beta_3$ RGD peptide binding region and formed similar kind of interactions with $Mn^{2+}$ and other amino acid residues. This supports the quality of the bound conformations of these antagonists predicted by our docking studies. Several discrepancies were found in the previously predicted binding orientations of RGD mimetic peptidomimetic and non peptide small-molecule antagonists.[43-47] Previously reported docking studies using non peptide small molecule antagonists also predicted very similar binding orientations to the orientation predicted in this study.[43, 45] However, docking studies performed on cyclic-RGD analogues and RGD mimetics produced binding orientations similar to the bound conformation of the cyclic RGD in the $\alpha_v\beta_3$-RGD complex crystal structure.[46, 47] The observed discrepancies between the predicted binding orientations of our novel antagonists and bound conformation of the cyclic RGD peptide in the $\alpha_v\beta_3$-RGD complex crystal structure are due to a significant structural difference between the cyclic RGD peptide and these novel antagonists. On the other hand, observed discrepancies may be a result of artifacts in our docking procedure. However, the high binding affinity (800-fold higher than parent AV26) exhibited by our most potent non-RGD mimetic antagonist AV38 could be explained by the novel binding interactions found in its predicted binding orientation. In this predicted binding orientation AV38 formed seven strong H-bonding interactions and a clear complementarity was found between chemical nature of its functional groups and various amino acid residues around its binding site on $\alpha_v\beta_3$. Further structural studies are warranted to explain the high binding affinity exerted by this non-RGD mimetic antagonist and its interactions with $\alpha_v\beta_3$.

Finally, in order to explain the recent discrepancy in the field between genetic results with knockout mice and the pharmacological effect with all reported antagonists, we refer to the model by Richard Hynes (FIG. 7), where he discusses the reason why genetically knocked out β3 integrin mice showed enhanced angiogenesis.[48] He argues that RGD peptides should be in fact referred to as "agonist" instead of "antagonist." If the word agonist is used, the genetic models are in accord with the pharmacological models. Although throughout this application we used the word "antagonist," as has been used in most previous reports, we are aware of the possibility that these compounds may be indeed acting as agonist. Whatever the mechanism, our compounds are highly potent and are very suitable for conjugation to various chemotherapeutic agents for selective delivery to $\alpha_v\beta_3$ positive cells.

Conclusions

Figure 7:
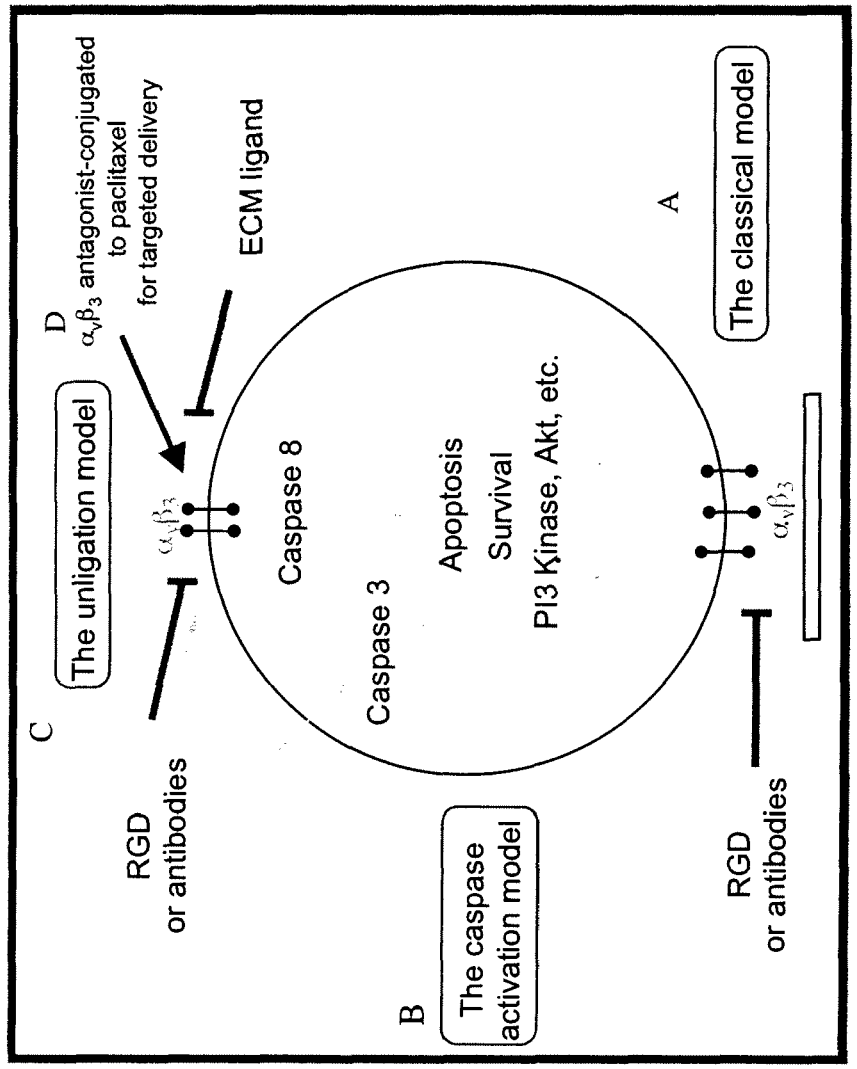
FIG. 7 illustrates four models for endothelial apoptosis. (a) The classical model, in which integrin engagement by ligand is necessary to provide survival signals. Inhibitors block ligand binding and thus the survival signals. (b) The caspase activation model, in which RGD peptides directly activate caspases and trigger apoptosis without any involvement of integrins. (c) The unligation model, or "integrin-mediated cell death," in which unligated integrins directly bind and activate caspase-8. ECM ligands block this, but RGD peptides and antibodies binding to the same integrins are not proposed to do so, even though they are known to activate integrins. (d) $\alpha_v\beta_3$ antagonists once conjugated to cytotoxic agents such as paclitaxel can be efficiently delivered to $\alpha_v\beta_3$ positive cancer cells and to the $\alpha_v\beta_3$ positive endothelial cells in tumor neovasculature (Modified from Richard Hynes, reference 48).

We have identified a series of structurally diverse integrin $\alpha_v\beta_3$ antagonists through the pharmacophore screening of a database of small-molecule drug-like compounds. The common features 3D pharmacophore models were generated utilizing a set of known integrin $\alpha_v\beta_3$ antagonists. The validated pharmacophore model successfully retrieved structurally novel compounds with high potency than the training set compounds that were used to generate the pharmacophore models. Furthermore, a limited structure-activity relationship analysis on one of the potent antagonists resulted in the discovery of highly potent compound with subnanomlar potency as non-RGD mimetic $\alpha_v\beta_3$ antagonists. These small-molecule antagonists possessing amenable structural scaffolds provide valuable leads for further optimization as potent non-RGD mimetic $\alpha_v\beta_3$ antagonists. We are conjugating three of the potent antagonists with paclitaxel as described in our recent manuscript.[41] Detailed pharmacological properties of these novel agents for targeted delivery to $\alpha_v\beta_3$ positive cancer cells will be presented (FIG. 7).

REFERENCES

1. Danen, E. H., Integrins: regulators of tissue function and cancer progression. *Curr Pharm Des* 2005, 11, (7), 881-91.
2. Humphries, M. J., Integrin structure. *Biochem Soc Trans* 2000, 28, (4), 311-39.
3. Martin, K. H.; Slack, J. K.; Boerner, S. A.; Martin, C. C.; Parsons, J. T., Integrin connections map: to infinity and beyond. *Science* 2002, 296, (5573), 1652-3.
4. Aplin, A. E.; Howe, A. K.; Juliano, R. L., Cell adhesion molecules, signal transduction and cell growth. *Curr Opin Cell Biol* 1999, 11, (6), 737-44.
5. Brooks, P. C.; Clark, R. A.; Cheresh, D. A., Requirement of vascular integrin alpha v beta 3 for angiogenesis. *Science* 1994, 264, (5158), 569-71.
6. Hood, J. D.; Cheresh, D. A., Role of integrins in cell invasion and migration. *Nat Rev Cancer* 2002, 2, (2), 91-100.
7. Felding-Habermann, B., Integrin adhesion receptors in tumor metastasis. *Clin Exp Metastasis* 2003, 20, (3), 203-13.
8. Natali, P. G.; Hamby, C. V.; Felding-Habermann, B.; Liang, B.; Nicotra, M. R.; Di Filippo, F.; Giannarelli, D.; Temponi, M.; Ferrone, S., Clinical significance of alpha(v) beta3 integrin and intercellular adhesion molecule-1 expression in cutaneous malignant melanoma lesions. *Cancer Res* 1997, 57, (8), 1554-60.
9. Felding-Habermann, B.; O'Toole, T. E.; Smith, J. W.; Fransvea, E.; Ruggeri, Z. M.; Ginsberg, M. H.; Hughes, P. E.; Pampori, N.; Shattil, S. J.; Saven, A.; Mueller, B. M., Integrin activation controls metastasis in human breast cancer. *Proc Natl Acad Sci USA* 2001, 98, (4), 1853-8.
10. Pecheur, I.; Peyruchaud, O.; Serre, C. M.; Guglielmi, J.; Voland, C.; Bourre, F.; Margue, C.; Cohen-Solal, M.; Buffet, A.; Kieffer, N.; Clezardin, P., Integrin alpha(v)beta3 expression confers on tumor cells a greater propensity to metastasize to bone. *Faseb J* 2002, 16, (10), 1266-8.
11. Kumar, C. C.; Armstrong, L.; Yin, Z.; Malkowski, M.; Maxwell, E.; Ling, H.; Yaremko, B.; Liu, M.; Varner, J.; Smith, E. M.; Neustadt, B.; Nechuta, T., Targeting integrins alpha v beta 3 and alpha v beta 5 for blocking tumor-induced angiogenesis. *Adv Exp Med Biol* 2000, 476, 169-80.
12. Shannon, K. E.; Keene, J. L.; Settle, S. L.; Duffin, T. D.; Nickols, M. A.; Westlin, M.; Schroeter, S.; Ruminski, P. G.; Griggs, D. W., Anti-metastatic properties of RGD-peptidomimetic agents S137 and S247. *Clin Exp Metastasis* 2004, 21, (2), 129-38.
13. Ruoslahti, E.; Pierschbacher, M. D., Arg-Gly-Asp: a versatile cell recognition signal. *Cell* 1986, 44, (4), 517-8.
14. Hynes, R. O., Integrins: versatility, modulation, and signaling in cell adhesion. *Cell* 1992, 69, (1), 11-25.
15. Kerr, J. S.; Wexler, R. S.; Mousa, S. A.; Robinson, C. S.; Wexler, E. J.; Mohamed, S.; Voss, M. E.; Devenny, J. J.; Czerniak, P. M.; Gudzelak, A., Jr.; Slee, A. M., Novel small molecule alpha v integrin antagonists: comparative anticancer efficacy with known angiogenesis inhibitors. *Anticancer Res* 1999, 19, (2A), 959-68.
16. Lark, M. W.; Stroup, G. B.; Hwang, S. M.; James, I. E.; Rieman, D. J.; Drake, F. H.; Bradbeer, J. N.; Mathur, A.; Erhard, K. F.; Newlander, K. A.; Ross, S. T.; Salyers, K. L.; Smith, B. R.; Miller, W. H.; Huffman, W. F.; Gowen, M., Design and characterization of orally active Arg-Gly-Asp peptidomimetic vitronectin receptor antagonist SB 265123 for prevention of bone loss in osteoporosis. *J Pharmacol Exp Ther* 1999, 291, (2), 612-7.
17. Reinmuth, N.; Liu, W.; Ahmad, S. A.; Fan, F.; Stoeltzing, O.; Parikh, A. A.; Bucana, C. D.; Gallick, G. E.; Nickols, M. A.; Westlin, W. F.; Ellis, L. M., Alphavbeta3 integrin antagonist S247 decreases colon cancer metastasis and angiogenesis and improves survival in mice. *Cancer Res* 2003, 63, (9), 2079-87.
18. Harms, J. F.; Welch, D. R.; Samant, R. S.; Shevde, L. A.; Miele, M. E.; Babu, G. R.; Goldberg, S. F.; Gilman, V. R.; Sosnowski, D. M.; Campo, D. A.; Gay, C. V.; Budgeon, L. R.; Mercer, R.; Jewell, J.; Mastro, A. M.; Donahue, H. J.; Erin, N.; Debies, M. T.; Meehan, W. J.; Jones, A. L.; Mbalaviele, G.; Nickols, A.; Christensen, N. D.; Melly, R.; Beck, L. N.; Kent, J.; Rader, R. K.; Kotyk, J. J.; Pagel, M. D.; Westlin, W. F.; Griggs, D. W., A small molecule antagonist of the alpha(v)beta3 integrin suppresses MDA-MB-435 skeletal metastasis. *Clin Exp Metastasis* 2004, 21, (2), 119-28.
19. Brooks, P. C.; Stromblad, S.; Klemke, R.; Visscher, D.; Sarkar, F. H.; Cheresh, D. A., Antiintegrin alpha v beta 3 blocks human breast cancer growth and angiogenesis in human skin. *J Clin Invest* 1995, 96, (4), 1815-22.
20. Brooks, P. C.; Montgomery, A. M.; Rosenfeld, M.; Reisfeld, R. A.; Hu, T.; Klier, G.; Cheresh, D. A., Integrin alpha v beta 3 antagonists promote tumor regression by inducing apoptosis of angiogenic blood vessels. *Cell* 1994, 79, (7), 1157-64.
21. Taga, T.; Suzuki, A.; Gonzalez-Gomez, I.; Gilles, F. H.; Stins, M.; Shimada, H.; Barsky, L.; Weinberg, K. I.; Laug, W. E., alpha v-Integrin antagonist EMD 121974 induces apoptosis in brain tumor cells growing on vitronectin and tenascin. *Int J Cancer* 2002, 98, (5), 690-7.
22. Mitjans, F.; Meyer, T.; Fittschen, C.; Goodman, S.; Jonczyk, A.; Marshall, J. F.; Reyes, G.; Piulats, J., In vivo therapy of malignant melanoma by means of antagonists of alphav integrins. *Int J Cancer* 2000, 87, (5), 716-23.

23. Allman, R.; Cowburn, P.; Mason, M., In vitro and in vivo effects of a cyclic peptide with affinity for the alpha(nu) beta3 integrin in human melanoma cells. *Eur J Cancer* 2000, 36, (3), 410-22.
24. Dechantsreiter, M. A.; Planker, E.; Matha, B.; Lohof, E.; Holzemann, G.; Jonczyk, A.; Goodman, S. L.; Kessler, H., N-Methylated cyclic RGD peptides as highly active and selective alpha(V)beta(3) integrin antagonists. *J Med Chem* 1999, 42, (16), 3033-40.
25. Burke, P. A.; DeNardo, S. J.; Miers, L. A.; Lamborn, K. R.; Matzku, S.; DeNardo, G. L., Cilengitide targeting of alpha (v)beta(3) integrin receptor synergizes with radioimmunotherapy to increase efficacy and apoptosis in breast cancer xenografts. *Cancer Res* 2002, 62, (15), 4263-72.
26. Rodan, S. B.; Rodan, G. A., Integrin function in osteoclasts. *J Endocrinol* 1997, 154 Suppl, S47-56.
27. Nakamura, I.; Pilkington, M. F.; Lakkakorpi, P. T.; Lipfert, L.; Sims, S. M.; Dixon, S. J.; Rodan, G. A.; Duong, L. T., Role of alpha(v)beta(3) integrin in osteoclast migration and formation of the sealing zone. *J Cell Sci* 1999, 112 (Pt 22), 3985-93.
28. Duong, L. T.; Rodan, G. A., The role of integrins in osteoclast function. *J Bone Miner Metab* 1999, 17, (1), 1-6.
29. Teitelbaum, S. L., Bone resorption by osteoclasts. *Science* 2000, 289, (5484), 1504-8.
30. Fisher, J. E.; Caulfield, M. P.; Sato, M.; Quartuccio, H. A.; Gould, R. J.; Garsky, V. M.; Rodan, G. A.; Rosenblatt, M., Inhibition of osteoclastic bone resorption in vivo by echistatin, an "arginyl-glycyl-aspartyl" (RGD)-containing protein. *Endocrinology* 1993, 132, (3), 1411-3.
31. Engleman, V. W.; Nickols, G. A.; Ross, F. P.; Horton, M. A.; Griggs, D. W.; Settle, S. L.; Ruminski, P. G.; Teitelbaum, S. L., A peptidomimetic antagonist of the alpha(v) beta3 integrin inhibits bone resorption in vitro and prevents osteoporosis in vivo. *J Clin Invest* 1997, 99, (9), 2284-92.
32. Yamamoto, M.; Fisher, J. E.; Gentile, M.; Seedor, J. G.; Leu, C. T.; Rodan, S. B.; Rodan, G. A., The integrin ligand echistatin prevents bone loss in ovariectomized mice and rats. *Endocrinology* 1998, 139, (3), 1411-9.
33. Hutchinson, J. H.; Halezenko, W.; Brashear, K. M.; Breslin, M. J.; Coleman, P. J.; Duong le, T.; Fernandez-Metzler, C.; Gentile, M. A.; Fisher, J. E.; Hartman, G. D.; Huff, J. R.; Kimmel, D. B.; Leu, C. T.; Meissner, R. S.; Merkle, K.; Nagy, R.; Pennypacker, B.; Perkins, J. J.; Prueksaritanont, T.; Rodan, G. A.; Varga, S. L.; Wesolowski, G. A.; Zartman, A. E.; Rodan, S. B.; Duggan, M. E., Nonpeptide alphavbeta3 antagonists. 8. In vitro and in vivo evaluation of a potent alphavbeta3 antagonist for the prevention and treatment of osteoporosis. *J Med Chem* 2003, 46, (22), 4790-8.
34. Murphy, M. G.; Cerchio, K.; Stoch, S. A.; Gottesdiener, K.; Wu, M.; Recker, R., Effect of L-000845704, an alphaVbeta3 integrin antagonist, on markers of bone turnover and bone mineral density in postmenopausal osteoporotic women. *J Clin Endocrinol Metab* 2005, 90, (4), 2022-8.
35. Pfaff, M.; Tangemann, K.; Muller, B.; Gurrath, M.; Muller, G.; Kessler, H.; Timpl, R.; Engel, J., Selective recognition of cyclic RGD peptides of NMR defined conformation by alpha IIb beta 3, alpha V beta 3, and alpha 5 beta 1 integrins. *J Biol Chem* 1994, 269, (32), 20233-8.
36. Burgess, K.; Lim, D.; Mousa, S. A., Synthesis and solution conformation of cyclo[RGDRGD]: a cyclic peptide with selectivity for the alpha V beta 3 receptor. *J Med Chem* 1996, 39, (22), 4520-6.
37. Xiong, J. P.; Stehle, T.; Zhang, R.; Joachimiak, A.; Frech, M.; Goodman, S. L.; Arnaout, M. A., Crystal structure of the extracellular segment of integrin alpha Vbeta3 in complex with an Arg-Gly-Asp ligand. *Science* 2002, 296, (5565), 151-5.
38. Xiong, J. P.; Stehle, T.; Diefenbach, B.; Zhang, R.; Dunker, R.; Scott, D. L.; Joachimiak, A.; Goodman, S. L.; Arnaout, M. A., Crystal structure of the extracellular segment of integrin alpha V beta3. *Science* 2001, 294, (5541), 339-45.
39. Marugan, J. J.; Manthey, C.; Anaclerio, B.; Lafrance, L.; Lu, T.; Markotan, T.; Leonard, K. A.; Crysler, C.; Eisennagel, S.; Dasgupta, M.; Tomczuk, B., Design, synthesis, and biological evaluation of novel potent and selective alphavbeta3/alphavbeta5 integrin dual inhibitors with improved bioavailability. Selection of the molecular core. *J Med Chem* 2005, 48, (4), 926-34.
40. *Catalyst* 4.9, Accelrys Inc: San Diego, USA, 2004.
41. Chen, X.; Plasencia, C.; Hou, Y.; Neamati, N., Synthesis and biological evaluation of dimeric RGD peptide-paclitaxel conjugate as a model for integrin-targeted drug delivery. *J Med Chem* 2005, 48, (4), 1098-106.
42. *GOLD* 1.2, CCDC: Cambridge, UK., 2002.
43. Gottschalk, K. E.; Gunther, R.; Kessler, H., A three-state mechanism of integrin activation and signal transduction for integrin alpha(v)beta(3). *Chembiochem* 2002, 3, (5), 470-3.
44. Gottschalk, K. E.; Kessler, H., The structures of integrins and integrin-ligand complexes: implications for drug design and signal transduction. *Angew Chem Int Ed Engl* 2002, 41, (20), 3767-74.
45. Feuston, B. P.; Culberson, J. C.; Duggan, M. E.; Hartman, G. D.; Leu, C. T.; Rodan, S. B., Binding model for nonpeptide antagonists of alpha(v)beta(3) integrin. *J Med Chem* 2002, 45, (26), 5640-8.
46. Marinelli, L.; Lavecchia, A.; Gottschalk, K. E.; Novellino, E.; Kessler, H., Docking studies on alphavbeta3 integrin ligands: pharmacophore refinement and implications for drug design. *J Med Chem* 2003, 46, (21), 4393-404.
47. Moitessier, N.; Henry, C.; Maigret, B.; Chapleur, Y., Combining pharmacophore search, automated docking, and molecular dynamics simulations as a novel strategy for flexible docking. Proof of concept: docking of arginine-glycine-aspartic acid-like compounds into the alphavbeta3 binding site. *J Med Chem* 2004, 47, (17), 4178-87.
48. Hynes, R. 0., A reevaluation of integrins as regulators of angiogenesis. *Nat Med* 2002, 8, (9), 918-21.
49. Smellie, A.; Kahn, S. D.; Teig, S. L., Analysis of Conformational Coverage 1. Validation and Estimation of Coverage. *J Chem Inf Comput Sci* 1995, 35, (2), 285-294.
50. Smellie, A.; Kahn, S. D.; Teig, S. L., Analysis of Conformational Coverage 2. Application of Conformational Models. *J Chem Inf Comput Sci* 1995, 35, (2), 295-304.
51. Smellie, A.; Teig, S. L.; Towbin, P., Poling—Promoting Conformational Variation. *J Comput Chem* 1995, 16, (2), 171-187.
52. Jones, G.; Willett, P.; Glen, R. C.; Leach, A. R.; Taylor, R., Development and validation of a genetic algorithm for flexible docking. *J Mol Biol* 1997, 267, (3), 727-48.
53. Nissink, J. W.; Murray, C.; Hartshorn, M.; Verdonk, M. L.; Cole, J. C.; Taylor, R., A new test set for validating predictions of protein-ligand interaction. *Proteins* 2002, 49, (4), 457-71.
54. Plasencia, C.; Dayam, R.; Wang, Q.; Pinski, J.; Burke, T. R., Jr.; Quinn, D. I.; Neamati, N., Discovery and preclinical evaluation of a novel class of small-molecule compounds in hormone-dependent and -independent cancer cell lines. *Mol Cancer Ther* 2005, 4, (7), 1105-13.

Example II

NVX-188 (AV38) Studies

Steric Interaction of NVX-188 and $\alpha_v\beta_3$ Integrin

Figure 9:
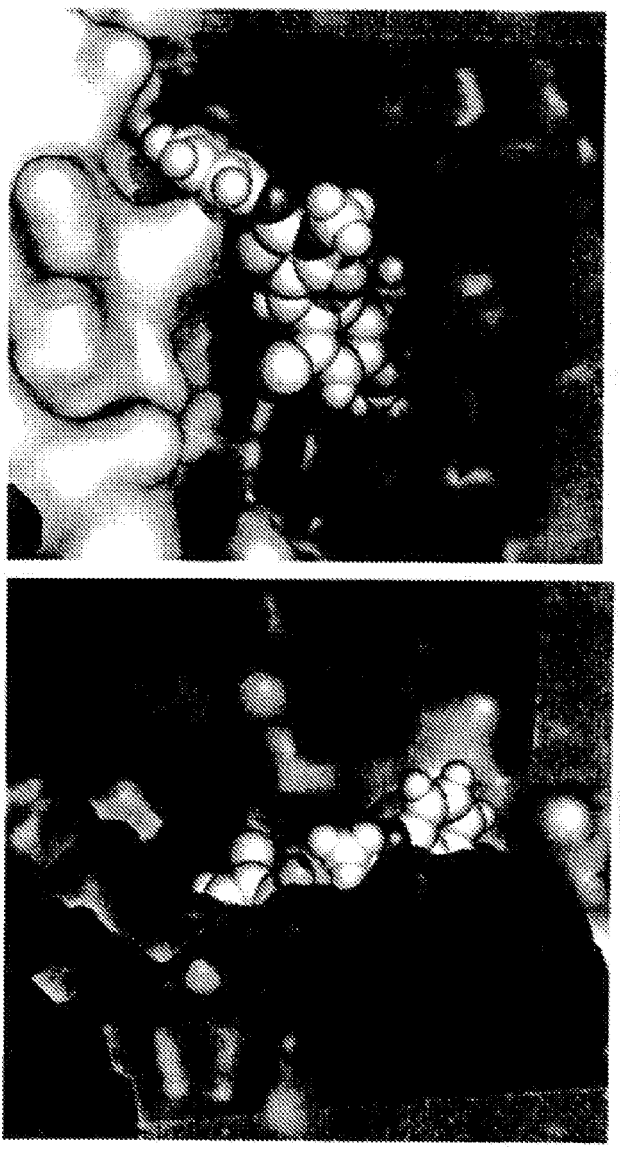
FIG. 9 illustrates the predicted bound conformation of NVX-188.

NVX-188 represents a novel, non-RGD mimetic class of $\alpha_v\beta_3$ antagonists. Docking configurations of NVX-188 with $\alpha_v\beta_3$ integrin were modeled using the GOLD software package. As can be seen in FIG. 9, the minimum energy docking conformation of NVX-188 and $\alpha_v\beta_3$ integrin shows NVX-188 occupying a groove at the active binding site near the junction of the two sub-chains.

Figure 10:
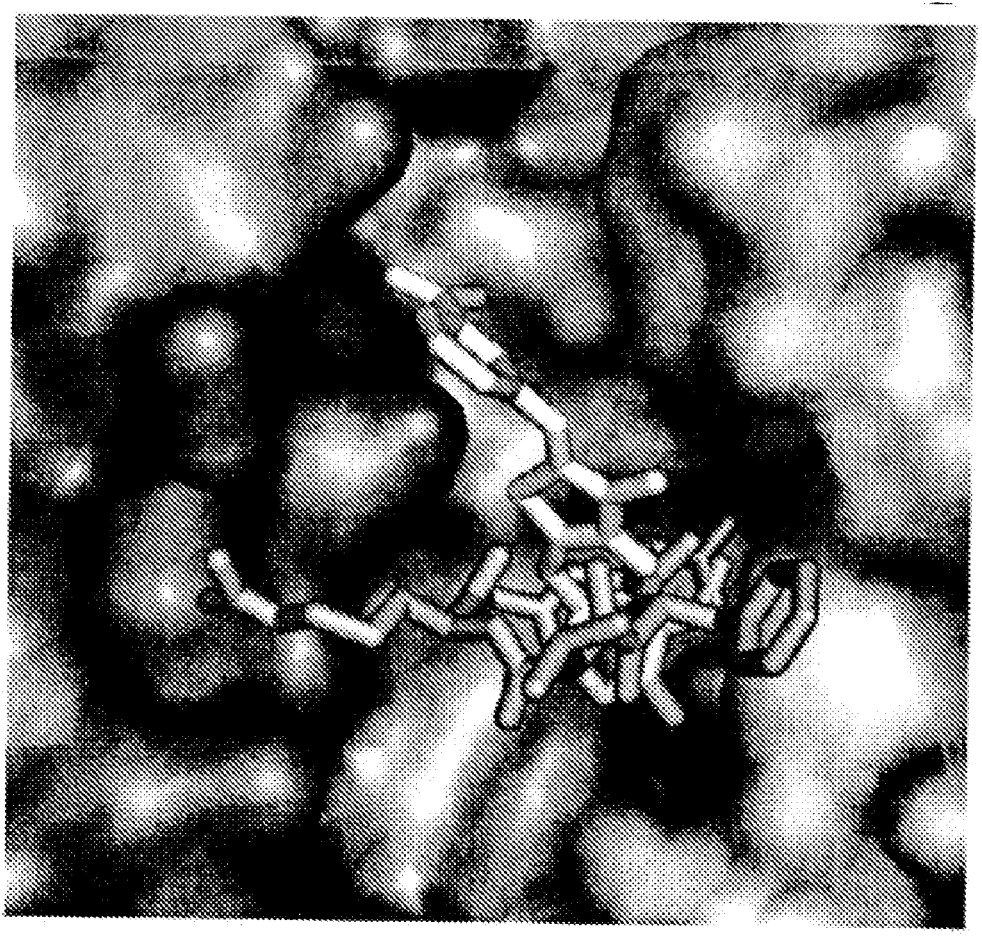
FIG. 10 illustrates the predicted docking of NVX-188 (aqua) and the RGD tripeptide (mauve) on $\alpha_v\beta_3$ integrin.

An alternative representation, in FIG. 10, shows the predicted docking of NVX-188 (aqua) in relation to the extracellular ligand protein's (mauve) RGD peptide's predicted position. The red sphere represents a $Mn^{2+}$ ion that is embedded in the $\alpha_v\beta_3$ integrin's active binding region. With NVX-188 in this conformation, the RGD tripeptide binding site is effectively blocked. Functional assays are needed to determine how NVX-188 binding to $\alpha_v\beta_3$ integrin affects the integrin's biological function. The observation that NVX-188 does not directly mimic the RGD peptide in its steric interactions with $\alpha_v\beta_3$ integrin suggests that NVX-188 will act as an antagonist (blocking agent) rather than an agonist (activating agent). It is the small molecule's orientation, relative to the $\alpha_v\beta_3$ receptor and to its RGD binding site, that characterizes the NVX-188 class of $\alpha_v\beta_3$ binding agents as novel and distinct.

NVX-188 is remarkable in its binding affinity for the $\alpha_v\beta_3$ integrin receptor, being active at picomolar concentrations. Other compounds in the NVX-188 class, identified during NVX-188 development (see above), showed substantially lower affinity. Their affinities were more in line with the affinities reported in the literature for known $\alpha_v\beta_3$ integrin antagonists.

Figure 11:
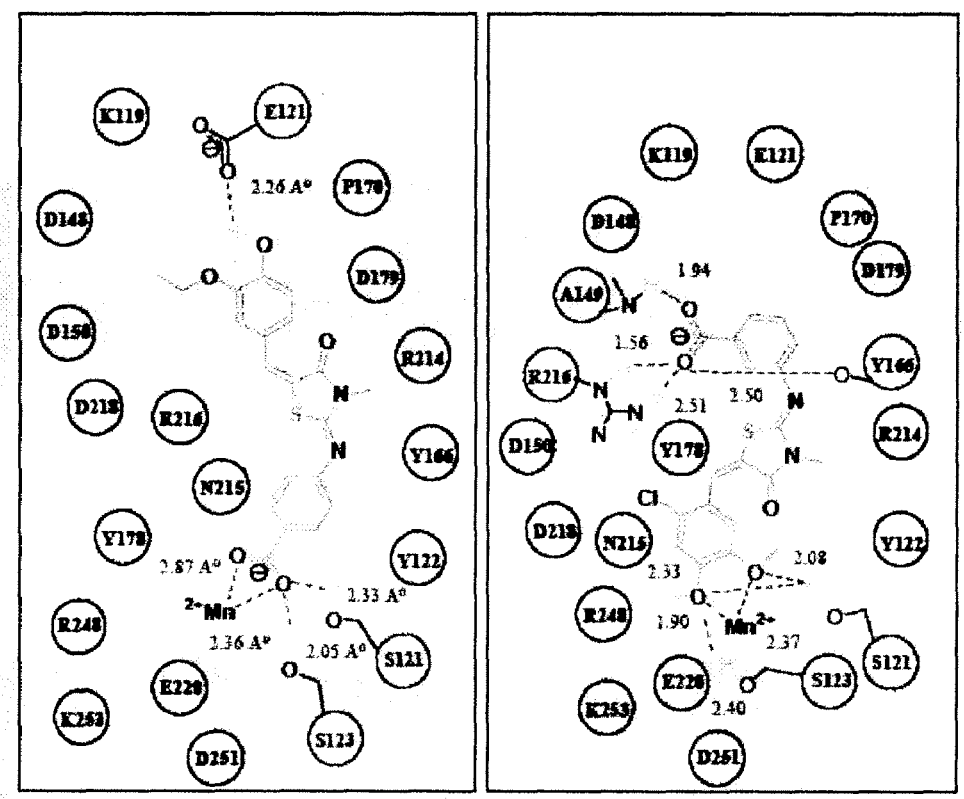
FIG. 11 illustrates the relationship of NVX-188 (right) and a prototypic RGD-mimetic small molecule (left) to amino acids in the $\alpha_v\beta_3$ heterodimer.

The basis for NVX-188's high affinity is apparent from FIG. 11. FIG. 11 shows the hydrogen bonds formed between NVX-188 and amino acids in the $\alpha_v\beta_3$ heterodimer. The high binding affinity of NVX-188 (see below) may be attributed to the relatively large number of hydrogen bonds formed between the small molecule and the protein.

$\alpha_v\beta_3$ Binding Affinity

Receptor binding affinity of NVX-188 was determined through a competitive binding experiment using $^{125}$I-radiolabeled echistatin on NCI-H1975 cells. Increasing concentrations of NVX-188 were added with a fixed amount of echistatin to determine the concentration of NVX-188 that prevents 50% of the echistatin from binding to $\alpha_v\beta_3$ integrin on the cell surface (i.e., $IC_{50}$).

The $\alpha_v\beta_3$ integrin/NVX-188 binding affinity was determined to be 0.03 nM (30 pM). It is useful to compare this to other reported $\alpha_v\beta_3$ antagonists described in the literature (such as SmithKline Beecham's SB223245) that generally show binding in the nanomaolar range.

Cytotoxicity Assay

NVX-188 was tested for cytotoxicity by MTT assays in two breast cancer cell lines, MDA-MB-435 with high $\alpha_v\beta_3$ integrin expression and MCF7 with low $\alpha_v\beta_3$ integrin expression, and an ovarian cancer cell line, HEY, which was used to test for cell growth inhibition evidence. NVX-188 was further evaluated in a lung cancer cell line, NCI-H1975, and a mouse fibroblast, NIH3T3. NVX-188 was not cytotoxic at the highest dose level tested (20 uM).

TABLE B

NVX-188 Cytotoxicity Assay.

|  | Cell line | Cytotoxicity (IC50) |
|---|---|---|
| Breast cancer | MDA-MB-435 | >20 uM |
| Breast cancer | MCF7 | >20 uM |
| Ovarian cancer | HEY | >20 uM |
| Lung cancer | NCI-H1975 | >20 uM |
| Mouse fibroblast | NIH3T3 | >20 uM |

Example III

A Novel Class of $\alpha_v\beta_3$ Antagonists for Treatment of Rheumatoid Arthritis Background A central role of $\alpha_v\beta_3$ integrin in rheumatoid arthritis. Integrins, a family of transmembrane adhesion receptors are principal mediators of cell attachment, migration, differentiation and survival.[1] Integrins are heterodimeric proteins that are composed of one $\alpha$- and one $\beta$-subunit, respectively, which associate non-covalently in defined combinations. To date at least 18 different $\alpha$- and 8 $\beta$-subunits have been identified, forming at least 24 functionally diverse integrins. The integrin $\alpha_v\beta_3$, also known as the vitronectin receptor, consists of a 125 kDa $\alpha_v$ subunit and a 105 kDa $\beta_3$ subunit. It has been the focus of intensive research because of its major role in several distinct pathophysiological processes which are particularly relevant for rheumatoid arthritis and for other diseases associated with neovascularisation, inflammation, and increased osteoclast activity. In addition to their well-described function for cell adhesion, $\alpha_v\beta_3$ integrins modulate various signaling pathways (MAP-kinase, Akt-kinase, VEGFR, and others), thereby affecting proliferation and apoptosis of osteoclasts, endothelial cells, as well as tumor cells.[3-12] The $\alpha_v\beta_3$ receptor binds to a variety of extracellular matrix proteins (ECM), including fibrinogen, vitronectin, osteopontin, and thrombospondin, largely through interaction with the Arg-Gly-Asp (RGD) tripeptide sequence.[13,14] Based on the sequence of this ligand-binding motif, a variety of peptidomimetic small molecule $\alpha_v\beta_3$ antagonists have been synthesized with activity in various disease models.[12,15-25] The $\alpha_v\beta_3$ receptor plays a pivotal role in bone resorption by osteoclasts and $\alpha_v\beta_3$ antagonists were shown to inhibit bone resorption in vivo without notable adverse affects.[26-34] Taken together, the role of integrin $\alpha_v\beta_3$ has been most extensively studied in the context of osteoclastogenesis and bone resorption, macrophage migration and activation, and angiogenesis. $\alpha_v\beta_3$ is over-expressed on activated macrophages and osteoclasts which are found in high numbers at sites of bone destruction in rheumatoid arthritis patients. In these patients, mature osteoclast numbers are highly associated with both periarticular and systemic bone loss. A substantial amount of evidence including data from animal arthritis models now exists to support the view that $\alpha_v\beta_3$ plays an important, if not decisive, role in activated macrophage dependent inflammation, osteoclast development and migration, bone resorption, as well as inflammatory angiogenesis. This evidence and a lack of efficient therapeutic options for the advanced stages of rheumatoid disease therefore strongly support the vision that development of novel compounds targeting $\alpha_v\beta_3$ is a highly rational, selective, and potential effective approach for this disease.[35]

Discovery of a Novel Class of $\alpha_v\beta_3$ Antagonists

Preliminary data. We have recently discovered a series of novel small-molecule $\alpha_v\beta_3$ antagonists utilizing chemical function-based common feature pharmacophore models.[36] Three-dimensional pharmacophore models were generated using a training set of three recently reported $\alpha_v\beta_3$ receptor antagonists. Upon validation using a chemical database of known antagonists of the $\alpha_v\beta_3$ receptor, a pharmacophore model with high discriminative ability was used as a three-dimensional query to retrieve compounds with novel structural scaffolds and desired chemical features. A computerized search of a chemical database of over 600,000 compounds yielded more than 800 compounds with structural features highly characteristic for $\alpha_v\beta_3$ antagonists. On the basis of structural novelty and calculated physicochemical and drug-like properties, a panel of compounds was selected for further in vitro screening. Of 29 compounds finally tested in $\alpha_v\beta_3$ receptor-specific competitive binding assays, several compounds (Table 3 in Example I) displayed binding affinities in the nanomolar to picomolar range.[36] One of these compounds (AV38), which has been now designated NVX-188, was chosen as the lead compound, due to its high-affinity binding characteristics at picomolar concentrations.

Experimental Plan

Overview

General considerations and aims. As is evident from the preliminary data presented above, six compounds displaying high affinity binding characteristics and excellent "drug-like properties" have been identified. These compounds not only possess excellent specific-binding characteristics, but their mode of action is likely to be different from existing $\alpha_v\beta_3$ antagonists. While NVX-188 has been defined as the lead compound, it may nevertheless be possible that other compounds of this group might have more favourable functional properties in in vitro assays. A more detailed description of the group of lead compounds (Table 3 in Example I) was recently published by our group in the Journal of Medicinal Chemistry.[36] Cell-based assays which are critically dependent on $\alpha_v\beta_3$ functions may be utilized to further characterize these compounds. These assays provide the basis for effectively selecting the best candidate for further preclinical and clinical development. These lead compounds optimized in silico and evaluated in binding pilot studies may be tested, for example, employing the following in vitro and in vivo model systems:

In vitro studies with validated models for the most important target tissues of $\alpha_v\beta_3$ inhibitors:
  Primary human endothelial cells (HUVECs)
  Primary osteoclasts/osteoblasts
  Osteosarcoma (SAOS-2) cell line expressing $\alpha_v\beta_3$
In vivo studies focusing on obtaining key data on the pharmacokinetic and toxicological characteristics of the $\alpha_v\beta_3$ drug candidates in rats.

Materials and Methods

Novel $\alpha_v\beta_3$ inhibitor drug candidates. The novel drug candidates (NVX-188 and analogues) are synthesized by and purchased from ChemDiv (San Diego, Calif.). Compounds are stored as 1 mM stock solutions in DMSO at −20° C. until use.

Reagents and antibodies. Bovine gelatin, bovine plasma fibronectin, human plasma vitronectin, rat collagen I, BSA, murine laminin, and poly-L-lysine are from Sigma (Sigma-Aldrich Co.). Anti-human actin antibody is from Sigma. Function-blocking mAbs: FB12 (anti-$\alpha_1$), P1E6 (anti-$\alpha_2$), P1B5 (anti-$\alpha_3$), and LM609 (anti-$\alpha_v\beta_3$) are obtained from Chemicon (Temecula, Calif.); mAbs Lia1/2 (anti-$\beta_1$), mAb GI9 (anti-$\alpha_2$), Sam-1 (anti-$\alpha_5$), and GoH3 (anti-$\alpha_6$) are from Beckman Coulter (Nyon, Switzerland). Protease inhibitor mixture containing 4-(2-aminoethyl)-benzenesulfonyl fluoride, aprotinin, leupeptin, bestatin, pepstatin A, and E-64 are from Sigma. Echistatin is from Bachem California Inc. (Torrance, Calif.).

Cell culture and treatments. The human osteosarcoma cell line SAOS-2 is from the American Type Culture Collection (ATCC, Manassas, Va.) and currently in use in our laboratory. Of interest, it has been recently demonstrated that $\alpha_v\beta_3$ integrin expression may play a role in the metastatic potential of SAOS-2 cells by enhancing the ability of the cells to migrate specifically to the lung.[37] $\alpha_v\beta_3$ expression correlated with the metastatic potential of osteosarcoma cells and cell adhesion to vitronectin decreased after treatment with echistatin, a well described and potent $\alpha_v\beta_3$ antagonist. $\alpha_v\beta_3$ integrin may therefore be a potential new target for osteosarcoma. Normal human osteoblastic cells expressing $\alpha_v\beta_3$ are from Promocell (Heidelberg, Germany). PromoCell's osteoblast cell culture system was developed to provide normal human osteoblasts in combination with an optimised osteoblast growth medium and subculture reagents. Normal human endothelial cells (HUVEC) are from Promocell and cultured as suggested by the manufacturer. Osteoclast cell culture and osteoclast differentiation assays are described in more detail further below.

Capillary tube formation assay. For in-vitro assays of the effects of inhibitors on angiogenesis (extent of tube assembly), a commercially available assay kit from Chemicon may be used. This assay kit represents a simple model of angiogenesis in which the induction or inhibition of tube formation by exogenous signals can be easily monitored. For assaying inhibitors or stimulators of tube formation, the endothelial cell suspension is incubated with different concentrations of compound to be tested and then added to the cells to the top of a specialized matrix. When cultured on the matrix, which is a solid gel of basement proteins prepared from the Engelbreth Holm-Swarm (EHS) mouse tumor, endothelial cells align and form hollow tube-like structures. Tube formation is a multi-step process involving cell adhesion, migration, differentiation, and growth. The assay can be used to monitor the extent of tube assembly in the presence of $\alpha_v\beta_3$ inhibitors in various endothelial cells, e.g., human umbilical vein cells (HUVEC) or bovine capillary endothelial (BCE) cells.

Impact on $\alpha_v\beta_3$ signalling. To determine the effect of inhibitors on $\alpha_v\beta_3$ signalling, cells are trypsinized and suspended in medium containing 10% serum in the presence or absence of $\alpha_v\beta_3$-binding proteins with or without inhibitors. After different time points (5-30 min), total cellular protein is obtained and assays are performed. For immunoprecipitation assays of focal adhesion kinase (FAK), FAK is immunoprecipitated from 300 µg-1 mg of total protein. Finally, Western blotting is performed for phosphorylated tyrosine and FAK as described below. In related but separate experiments, HUVECs growing on vitronectin-coated flasks are incubated with or without 10 ng/ml VEGF for 1 h in 10% FBS-containing medium. Inhibitors are then added for 5-30 min, and protein is harvested from cell lysates. Western blot analysis is done for total and phosphorylated forms of VEGFR and Akt. Several reports indicate that the mitogen-activated protein kinases (MAPK) as well as the PI3-kinase signalling cascades are modulated by integrin inhibitors. Antibodies for investigating several steps within the MAPK and Akt signalling pathways are available from several companies (e.g., Cell Signalling and Upstat). Different antibodies representing various phosphorylation (activation) states are also available (from Cell Signalling and/or Upstat) and may be used on total lysates as well as for immunohistochemical analysis.

Cell adhesion assays and coating. Endothelial cells are collected by trypsin digestion and seeded in serum-free M199 medium at $2 \times 10^4$ cells/well (96-well plate) or at $1-2 \times 10^5$ cells/well on 12 or 24-well plates. Blocking anti-integrin-mAbs are added at this step (at 10 µg/ml). After 1 h at 37° C., cells are gently washed with PBS and attached cells fixed in 4% paraformaldehyde (Fluka Chemie, Buchs, Switzerland) and stained with 0.5% crystal violet. Absorbance of each well is read at 620 nm in a plate reader. Results are expressed as the mean value±S.D of triplicate determinations. Culture plates are pre-coated, depending on the type of experiment, with fibronectin (3 µg/ml), gelatin (0.5%), collagen I (10 µg/ml), laminin (10 µg/ml), or vitronectin (1 µg/ml) in PBS for 1 h at 37° C. Then they are blocked with 0.5% heat inactivated fatty acid free bovine serum albumin for 1 hour at 37° C. and washed in Phosphate Buffered Saline (PBS). In experiments where ECM proteins are added in solution, cells are collected by trypsin treatment, washed with PBS, and resuspended in serum-free M199 medium and incubated for 1-2 h at 37° C. ECM proteins are then added at the concentrations indicated above, and cells are further incubated in suspension for another 30 to 60 min. To determine the effect of inhibitors on cell attachment, cells are seeded on 96-well plates with or without inhibitors. After 60 min, cells are washed, and attached cells are counted.

Proliferation, apoptosis, and clonogenic cell death of treated cells. HUVEC, osteosarcoma cells, and osteoblasts are plated on ECM protein-coated (vitronectin, fibrinogen, osteopontin, depending on the cell type) flasks and incubated for 48 h to a final confluence of 60-80% in serum-containing medium. Inhibitors are added concomitantly to appropriate concentrations. Floating and attached cells are harvested after 8 and 24 h of treatment, resuspended in medium containing serum and counted. Apoptosis is determined by staining with Hoechst dye. For ECMP-coated plates, inhibitors are added 3 hours after seeding when the cells are well attached and spread. Briefly, after the end of the treatment, both floating and attached cells are collected, incubated in experimental medium enriched in FCS for 1 hour at 37° C., then subjected to annexin V/propidium iodide (PI) staining using annexin V-Alexa Fluor 488 from Molecular Probes and PI from Sigma. The resulting fluorescence is measured by flow cytometry. Staining cells with a combination of annexin V and PI allows determining non-apoptotic cells (annexin V−/PI−), early apoptotic cells (annexin V+/PI−), late apoptotic cells (annexin V+/PI+), as well as necrotic cells (annexin V−/PI+). Cell counting and viability determination are performed by trypan blue exclusion.

SDS PAGE and Western blotting. Following the indicated treatment, cells are lysed in Laemmli buffer containing 4% SDS, 20% glycerol and 200 mM Tris, pH 6.8. Protein concentrations are determined using the BCA assay (Sigma). Equal amounts of total protein are separated by SDS-PAGE and then blotted onto PVDF or Nitrocellulose membranes, depending on the primary antibody. Membranes were blocked with 5% skimmed milk in PBS and then hybridized with the primary antibody of interest. Membranes are washed in PBS and then hybridized with the appropriate secondary antibody. Anti-mouse and anti-rabbit peroxidase- or alkaline phosphatase-conjugated secondary antibodies are diluted in PBS containing 5% skimmed milk. After washing with PBS, immune complexes on membranes are detected by enhanced chemiluminescence (Pierce, Rockford, Ill., USA).

Preparation of osteoclasts for ex vivo determination of osteoclastogenesis. Osteoclasts are obtained from mouse spleens by homogenizing up to two spleens in 5 ml PBS using a nylon mash (70 µm). Cells are then transferred into 15 ml tubes and collected by centrifuging at 1200 U/min for 10 min. After washing in PBS, cells are resuspended in 15 ml alpha MEM (10% PBS) with 30 ng/ml M-CSF, cultured o.n. at 37° C. and harvested. After washing in PBS, cells are placed in 30 ml total volume over 15 ml Ficoll and centrifuged at 1420 U/min at 8° C. for 30 min. Cells in the interphase are collected, washed twice in PBS, resuspended and counted. Appropriate numbers of cells are then plated in 48-well plates in the presence or absence of modulators of $\alpha_v\beta_3$ signaling and/or receptor binding. For determination of effects of inhibitors on osteoclast differentiation, mouse spleen cells are plated overnight and non-adherent cells are recovered and plated in 24 well plates ($10^6$ cells per well) in the presence of M-CSF (20 ng/ml), and in the presence or absence of inducers, for example RANKL (50 ng/ml) with or without specific inhibitors of $\alpha_v\beta_3$ integrin. The extent of osteoclast differentiation are then evaluated after 4 days of culture by TRAP staining using the Leukocyte Acid Phosphatase kit. All TRAP-positive cells with 3 or more nuclei are counted as osteoclasts.

Pharmacokinetic and toxicology studies. In short, a basic extraction and LC-MS or LC-MS/MS analytical method will be used for each compound. The pharmacokinetic study is performed for oral and intravenous administration with the compounds. Following dosing, blood will be collected at seven time points (0.5, 1, 2, 4, 6, 8, and 12 hours) for each rat treated by oral route and nine time points (5 min, 15 min, 30 min and 1, 2, 4, 6, 8, and 12 hours). Pharmacokinetic parameters ($C_{max}$, $T_{max}$, $V_d$, and bioavailability) are determined for individual rats using non-compartmental analysis using WinNonlin (Pharsight Corp). In addition, global blood count and liver and renal blood parameters are determined for each animal treated.

REFERENCES

1. Danen E H. Integrins: regulators of tissue function and cancer progression. Curr Pharm Des 2005, 11: 881-91.
2. Humphries M J. Integrin structure. Biochem Soc Trans 2000, 28: 311-39.
3. Martin K H, Slack J K, Boerner S A, Martin C C, Parsons J T. Integrin connections map: to infinity and beyond. Science 2002, 296: 652-53.
4. Aplin A E, Howe A K, Juliano R L. Cell adhesion molecules, signal transduction and cell growth. Curr Opin Cell Biol 1999, 11: 737-44.
5. Brooks P C, Clark R A, Cheresh D A. Requirement of vascular integrin alpha v beta 3 for angiogenesis. Science 1994, 264: 569-71.
6. Hood J D, Cheresh D A. Role of integrins in cell invasion and migration. Nat Rev Cancer 2002, 2: 91-100.
7. Felding-Habermann B. Integrin adhesion receptors in tumor metastasis. Clin Exp Metastasis 2003, 20: 203-13.
8. Natali P G, Hamby C V, Felding-Habermann B, et al. Clinical significance of alpha(v)beta3 integrin and intercellular adhesion molecule-1 expression in cutaneous malignant melanoma lesions. Cancer Res 1997, 57: 1554-60.
9. Felding-Habermann B, O'Toole T E, Smith J W, et al. Integrin activation controls metastasis in human breast cancer. Proc Natl Acad Sci USA 2001, 98: 1853-58.
10. Pecheur I, Peyruchaud O, Serre C M, et al. Integrin alpha (v)beta3 expression confers on tumor cells a greater propensity to metastasize to bone. Faseb J 2002, 16: 1266-68.
11. Kumar C C, Armstrong L, Yin Z, et al. Targeting integrins alpha v beta 3 and alpha v beta 5 for blocking tumor-induced angiogenesis. Adv Exp Med Biol 2000, 476: 169-80.

12. Shannon K E, Keene J L, Settle S L, et al. Anti-metastatic properties of RGD peptidomimetic agents S137 and S247. Clin Exp Metastasis 2004, 21: 129-38.
13. Ruoslahti E, Pierschbacher M D. Arg-Gly-Asp: a versatile cell recognition signal. Cell 1986, 44: 517-18.
14. Hynes R O. Integrins: versatility, modulation, and signaling in cell adhesion. Cell 1992, 69: 11-25.
15. Kerr J S, Wexler R S, Mousa S A, et al. Novel small molecule alpha v integrin antagonists: comparative anticancer efficacy with known angiogenesis inhibitors. Anticancer Res 1999, 19: 959-68.
16. Lark M W, Stroup G B, Hwang S M, et al. Design and characterization of orally active Arg-Gly-Asp peptidomimetic vitronectin receptor antagonist SB 265123 for prevention of bone loss in osteoporosis. J Pharmacol Exp Ther 1999, 291: 612-17.
17. Reinmuth N, Liu W, Ahmad S A, et al. Alphavbeta3 integrin antagonist S247 decreases colon cancer metastasis and angiogenesis and improves survival in mice. Cancer Res 2003, 63: 2079-87.
18. Harms J F, Welch D R, Samant R S, et al. A small molecule antagonist of the alpha(v)beta3 integrin suppresses MDA-MB-435 skeletal metastasis. Clin Exp Metastasis 2004, 21: 119-28.
19. Brooks P C, Stromblad S, Klemke R, Visscher D, Sarkar F H, Cheresh D A. Antiintegrin alpha v beta 3 blocks human breast cancer growth and angiogenesis in human skin. J Clin Invest 1995, 96: 1815-22.
20. Brooks P C, Montgomery A M, Rosenfeld M, Reisfeld R A, Hu T, Klier G, Cheresh D A. Integrin alpha v beta 3 antagonists promote tumor regression by inducing apoptosis of angiogenic blood vessels. Cell 1994, 79: 1157-64.
21. Taga T, Suzuki A, Gonzalez-Gomez I, et al. alpha v-Integrin antagonist EMD 121974 induces apoptosis in brain tumor cells growing on vitronectin and tenascin. Int J Cancer 2002, 98: 690-97.
22. Mitjans F, Meyer T, Fittschen C, Goodman S, Jonczyk A, Marshall J F, Reyes G, Piulats J. In vivo therapy of malignant melanoma by means of antagonists of alphav integrins. Int J Cancer 2000, 87: 716-23.
23. Allman R, Cowburn P, Mason M. In vitro and in vivo effects of a cyclic peptide with affinity for the alpha (nu) beta3 integrin in human melanoma cells. Eur J Cancer 2000, 36: 410-22.
24. Dechantsreiter M A, Planker E, Matha B, Lohof E, Holzemann G, Jonczyk A, Goodman S L, Kessler H. N-Methylated cyclic RGD peptides as highly active and selective alpha(V)beta(3) integrin antagonists. J Med Chem 1999, 42: 3033-40.
25. Burke P A, DeNardo S J, Miers L A, Lamborn K R, Matzku S, DeNardo G L. Cilengitide targeting of alpha(v) beta(3) integrin receptor synergizes with radioimmunotherapy to increase efficacy and apoptosis in breast cancer xenografts. Cancer Res 2002, 62: 4263-72.
26. Rodan S B, Rodan G A. Integrin function in osteoclasts. J Endocrinol 1997, 154 (Suppl.): 47-56.
27. Nakamura I, Pilkington M F, Lakkakorpi P T, Lipfert L, Sims S M, Dixon S J, Rodan G A, Duong L T. Role of alpha(v)beta(3) integrin in osteoclast migration and formation of the sealing zone. J Cell Sci 1999, 112: 3985-93.
28. Duong L T, Rodan G A. The role of integrins in osteoclast function. J Bone Miner Metab 1999, 17: 1-6.
29. Teitelbaum S L. Bone resorption by osteoclasts. Science 2000, 289: 1504-8.
30. Fisher J E, Caulfield M P, Sato M, Quartuccio H A, Gould R J, Garsky V M, Rodan, G A, Rosenblatt, M. Inhibition of osteoclastic bone resorption in vivo by echistatin, an "arginyl-glycyl-aspartyl" (RGD)-containing protein. Endocrinology 1993, 132: 1411-13.
31. Engleman V W, Nickols G A, Ross F P, Horton M A, Griggs D W, Settle S L, Ruminski P G, Teitelbaum S L. A peptidomimetic antagonist of the alpha(v)beta3 integrin inhibits bone resorption in vitro and prevents osteoporosis in vivo. J Clin Invest 1997, 99: 2284-92.
32. Yamamoto M, Fisher J E, Gentile M, Seedor J G, Leu C T, Rodan S B, Rodan G A. The integrin ligand echistatin prevents bone loss in ovariectomized mice and rats. Endocrinology 1998, 139: 1411-19.
33. Hutchinson J H, Halczenko W, Brashear K M, et al. Nonpeptide alphavbeta3 antagonists. In vitro and in vivo evaluation of a potent alphavbeta3 antagonist for the prevention and treatment of osteoporosis. J Med Chem 2003, 46: 4790-98.
34. Murphy M G, Cerchio K, Stoch S A, Gottesdiener K, Wu M, Recker R. Effect of L-000845704, an alphaVbeta3 integrin antagonist, on markers of bone turnover and bone mineral density in postmenopausal osteoporotic women. J Clin Endocrinol Metab 2005, 90: 2022-28.
35. Wilder R L. Integrin alpha V beta 3 as a target for treatment of rheumatoid arthritis and related rheumatic diseases. Ann Rheum Dis 2002, 61: 96-99.
36. Dayam R, Aiello F, Deng J, Wu Y, Garofalo A, Chen X, Neamati N. Discovery of small molecule integrin alphavbeta3 antagonists as novel anticancer agents. J Med Chem. 2006, 49: 4526-34.
37. Duan X, Jia S F, Zhou Z, Langley R R, Bolontrade M F, Kleinerman E S. Association of alphavbeta3 integrin expression with the metastatic potential and migratory and chemotactic ability of human osteosarcoma cells. Clin Exp Metastasis. 2004, 21: 747-53.

What is claimed is:

1. A composition comprising a pharmaceutically or cosmeceutically acceptable carrier and AV26

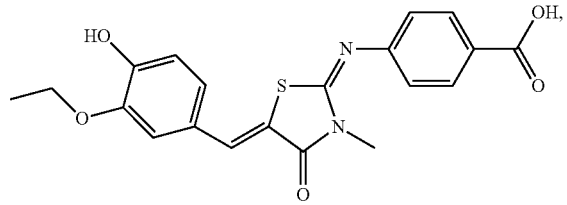

or a pharmaceutically or cosmeceutically acceptable salt, solvate, or hydrate thereof.

2. A composition comprising a pharmaceutically or cosmeceutically acceptable carrier and AV38

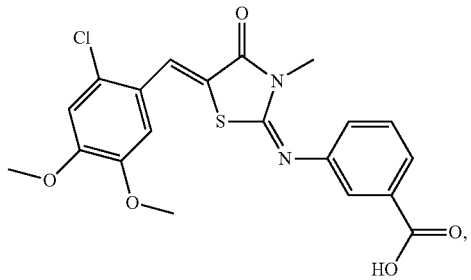

or a pharmaceutically or cosmeceutically acceptable salt, solvate, or hydrate thereof.

* * * * *